United States Patent
Moriya

(10) Patent No.: US 7,245,364 B2
(45) Date of Patent: Jul. 17, 2007

(54) APPARATUS FOR INSPECTING A SURFACE OF AN OBJECT TO BE PROCESSED

(75) Inventor: Tsuyoshi Moriya, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 104 days.

(21) Appl. No.: 11/171,236

(22) Filed: Jul. 1, 2005

(65) Prior Publication Data

US 2006/0001877 A1    Jan. 5, 2006

Related U.S. Application Data

(60) Provisional application No. 60/598,425, filed on Aug. 4, 2004.

(30) Foreign Application Priority Data

Jul. 2, 2004    (JP) .............................. 2004-197056

(51) Int. Cl.
*G01N 21/00* (2006.01)

(52) U.S. Cl. ................ 356/237.1; 356/237.5; 356/237.3; 356/237.4

(58) Field of Classification Search .. 356/237.1–237.5, 356/239.7–239.8, 30–31, 446, 364–369, 356/394, 239.1, 239.3, 625, 328, 630; 250/559.41, 250/225

See application file for complete search history.

(56) References Cited

U.S. PATENT DOCUMENTS

| | | | |
|---|---|---|---|
| 5,486,919 A | * | 1/1996 | Tsuji et al. ................. 356/484 |
| 2002/0122174 A1 | | 9/2002 | Hamamatsu et al. |
| 2004/0246476 A1 | * | 12/2004 | Bevis et al. ............. 356/237.5 |

FOREIGN PATENT DOCUMENTS

JP    9-210918    8/1997

* cited by examiner

*Primary Examiner*—Layla G. Lauchman
*Assistant Examiner*—Tri Ton
(74) *Attorney, Agent, or Firm*—Oblon, Spivak, McClelland, Maier & Neustadt, P.C.

(57) ABSTRACT

An apparatus for inspecting a surface of an object to be processed includes at least one irradiation unit for irradiating a light on the surface of the object; at least one detection unit for detecting a light scattered from the surface of the object in response to the irradiated light; and a determination unit for determining a cause of the scattered light based on the scattered light detected by the detection unit. The irradiation unit irradiates at least one irradiation light of s-polarization and p-polarization while varying an irradiation angle of the irradiated light. The determination unit determines whether the cause of the scattered light is a foreign material or a microscopic defect based on an intensity of the detected scattered light.

13 Claims, 15 Drawing Sheets

APPARATUS FOR INSPECTING A SURFACE OF AN OBJECT TO BE PROCESSED

CROSS-REFERENCE TO RELATED APPLICATIONS

This document claims priority to Japanese Patent Application No. 2004-197056, filed on Jul. 2, 2004 and U.S. Provisional Application No. 60/598,425, filed on Aug. 4, 2004, the entire content of which are hereby incorporated by reference.

FIELD OF THE INVENTION

The present invention relates to an apparatus for inspecting a surface of an object to be processed; and, more particularly, to an object surface inspection apparatus capable of determining whether a defect on a surface of a substrate is a foreign material or a microscopic defect.

BACKGROUND OF THE INVENTION

With regard to a semiconductor device such as a ULSI, if a particle-shaped foreign material (hereinafter, referred to as "particle") adheres to its surface, a short circuit may be caused, rendering the semiconductor device inoperable. Therefore, it is necessary to perform an inspection of whether a particle exists on a surface of the semiconductor device in a course of manufacturing it, for example, in a plasma processing system. Such inspection has been conventionally conducted by using an apparatus 150 for inspecting a surface of an object to be processed (hereinafter, referred to as "object surface inspection apparatus") using a laser scattering method, as shown in FIG. 15.

The object surface inspection apparatus 150 irradiates a laser beam to an inspection site on the surface of a wafer W mounted on a rotatable and vertically movable stage 151 from a laser beam illuminator 152 disposed above the stage slantwise. Then, a scattered light detector 153 disposed above the stage 151 detects a scattered light, which might be generated in case a particle adheres to the inspection site, and an operation unit 154 connected to the scattered light detector 153 analyzes the detected scattered light. If it is determined by the object surface inspection apparatus 150 that there exists a particle on the surface of the wafer W, the operation of a corresponding manufacturing line is stopped, and cleaning of the manufacturing line is performed in order to prevent a reduction in the yield of semiconductor devices in the manufacturing line.

At this time, a scratch, which is a polishing damage occurred on the surface of the wafer W, also generates a scattered light when a laser beam is irradiated thereto. Accordingly, even when there is no particle on the surface of the wafer W, the object surface inspection apparatus 150 erroneously determines that there is a particle due to the presence of the scratch. As a result, an unnecessary cleaning of the manufacturing line is performed, which decreases the operating rate of the manufacturing line.

For the above reason, there has been developed an object surface inspection apparatus capable of determining whether a defect on the wafer surface is a particle or a scratch. Known as such inspection apparatus is an object surface inspection apparatus using a dimensional characteristic of a scratch that it has a depth much smaller than its width (see, for example, US Patent Application Publication No. 2002/0122174 A1). This object surface inspection apparatus uses the fact that the quantity of scattered lights generated by an irradiation of an incident light to the scratch in a direction oblique to the wafer surface is smaller than the quantity of scattered lights generated by an irradiation of an incident light in a direction normal to the wafer surface.

However, as circuits formed on a semiconductor device become finer recently, the size of particles to be inspected is also becoming finer to the extent that they have the same size as microscopic defects (for example, voids or cracks) in a resist film formed on a wafer surface. Accordingly, it is necessary to distinguish the particles and the microscopic defects. Since, however, the microscopic defects have a depth substantially identical to or greater than its width and have a shape different from the scratch, the conventional object surface inspection apparatus cannot be used to distinguish the particle and the microscopic defect.

SUMMARY OF THE INVENTION

It is, therefore, an object of the present invention to provide an object surface inspection apparatus capable of distinguishing a foreign material and a microscopic defect on a surface of an object to be processed.

In accordance with one aspect of the present invention, there is provided an apparatus for inspecting a surface of an object to be processed, including: at least one irradiation unit for irradiating a light on the surface of the object; at least one detection unit for detecting a light scattered from the surface of the object in response to the irradiated light; and a determination unit for determining a cause of the scattered light based on the scattered light detected by the detection unit, wherein the irradiation unit irradiates at least one irradiation light of s-polarization and p-polarization while varying an irradiation angle of the irradiated light; and the determination unit determines whether the cause of the scattered light is a foreign material or a microscopic defect based on an intensity of the detected scattered light.

With such arrangements, at least one irradiation light of s-polarization and p-polarization is irradiated on the surface of the object to be processed while varying an irradiation angle of the irradiated light, and the determination unit determines whether the cause of the scattered light is a foreign material or a microscopic defect based on an intensity of the detected scattered light. The intensities of the scattered lights form the foreign material and microscopic defect due to the irradiation light of a specific polarization component are varied depending on the respective irradiation angles. Accordingly, by irradiating an irradiation light at an irradiation angle which renders the intensities of the scattered lights from the foreign material and the microscopic defect significantly different, it is possible to appropriately determine whether that on the surface of the object is a foreign material or a microscopic defect.

Preferably, the irradiation unit irradiates an irradiation light of s-polarization at a small irradiation angle, and the determination unit determines that the cause of the scattered light is the foreign material when the intensity of the detected scattered light is great and that the cause of the scattered light is the microscopic defect when the intensity of the detected scattered light is small. The intensity of the scattered light from the foreign material due to the s-polarization irradiation light of a small irradiation angle is greater than intensity of the scattered light from the microscopic defect due to the s-polarization irradiation light of a small irradiation angle. Accordingly, it is possible to positively determine whether that on the surface of the object is a foreign material or a microscopic defect.

Preferably, the irradiation unit irradiates irradiation lights of s-polarization and p-polarization, and the determination unit determines the cause of the scattered light based on a ratio of an intensity of the scattered light due to the irradiation light of s-polarization to an intensity of the scattered light due to the irradiation light of p-polarization. The above ratio from a foreign material is greater than that from a microscopic defect. Accordingly, it is possible to positively determine whether that on the surface of the object is a foreign material or a microscopic defect.

Preferably, the irradiation unit irradiates the irradiation lights at a small irradiation angle, and the determination unit determines that the cause of the scattered light is the foreign material when the above ratio is great and that the cause of the scattered light is the microscopic defect when the above ratio is small. As for the scattered light due to the irradiation light of small irradiation angle, the above ratio from a foreign material is significantly greater than that from a microscopic defect. Accordingly, it is possible to positively determine whether that on the surface of the object is a foreign material or a microscopic defect.

Preferably, the irradiation unit varies the irradiation angles of the irradiation lights from 15 to 45 degrees with respect to the surface of the object, and the determination unit determines that the cause of the scattered light is the foreign material when the ratio is greater than 1 and that the cause of the scattered light is the microscopic defect when the ratio is 1 or less. As for the irradiation angle of 15 to 45 degrees, the ratio from the microscopic defect is always 1 or less. Accordingly, it is possible to positively determine whether that on the surface of the object is a foreign material or a microscopic defect.

In accordance with another aspect of the present invention, there is provided an apparatus for inspecting a surface of an object to be processed, including: at least one irradiation unit for irradiating a light on the surface of the object; at least one detection unit for detecting a light scattered from the surface of the object in response to the irradiated light; and a determination unit for determining a cause of the scattered light based on the scattered light detected by the detection unit, wherein the irradiation unit is fixed to irradiate the light at an angle, and irradiates at least one irradiation light of s-polarization and p-polarization; and the determination unit determines whether the cause of the scattered light is a foreign material or a microscopic defect based on an intensity of the detected scattered light.

With such arrangements, the intensities of the scattered light from the foreign material and microscopic defect due to the irradiation light of a specific polarization are significantly different depending on irradiation angles. Accordingly, by setting the irradiation angle properly, it is possible to appropriately determine whether that on the surface of the object is a foreign material or a microscopic defect without varying the irradiation angle of the irradiation light, thereby simplifying the constructions of the object surface inspection apparatus.

Preferably, the irradiation unit is fixed to irradiate an irradiation light of s-polarization at a small irradiation angle, and the determination unit determines that the cause of the scattered light is the foreign material when the intensity of the detected scattered light is great and that the cause of the scattered light is the microscopic defect when the intensity of the detected scattered light is small. The intensity of the scattered light from the foreign material due to the s-polarization irradiation light of a small irradiation angle is greater than intensity of the scattered light from the microscopic defect due to the s-polarization irradiation light of a small irradiation angle. Accordingly, it is possible to positively determine whether that on the surface of the object is a foreign material or a microscopic defect.

Preferably, the irradiation unit irradiates irradiation lights of s-polarization and p-polarization, and the determination unit determines the cause of the scattered light based on a ratio of an intensity of the scattered light due to the irradiation light of s-polarization to an intensity of the scattered light due to the irradiation light of p-polarization. The above ratio from a foreign material is greater than that from a microscopic defect. Accordingly, it is possible to positively determine whether that on the surface of the object is a foreign material or a microscopic defect.

Preferably, the irradiation unit is fixed to irradiate the irradiation lights at a small irradiation angle, and the determination unit determines that the cause of the scattered light is the foreign material when the ratio is great and that the cause of the scattered light is the microscopic defect when the ratio is small. As for the scattered light due to the irradiation light of small irradiation angle, the above ratio from the foreign material is significantly greater than that from the microscopic defect. Accordingly, it is possible to positively determine whether that on the surface of the object is a foreign material or a microscopic defect.

Preferably, the irradiation unit is fixed to irradiate the irradiation lights at any angle of 15 to 45 degrees with respect to the surface of the object, and the determination unit determines that the cause of the scattered light is the foreign material when the ratio is greater than 1 and that the cause of the scattered light is the microscopic defect when the ratio is 1 or less. The above ratio from the microscopic defect at the irradiation angle of 15 to 45 degrees is always 1 or less. Accordingly, it is possible to positively determine whether that on the surface of the object is a foreign material or a microscopic defect.

In accordance with still another aspect of the present invention, there is provided an apparatus for inspecting a surface of an object to be processed, including: at least one irradiation unit for irradiating a light on the surface of the object; at least one detection unit for detecting a light scattered from the surface of the object in response to the irradiated light; and a determination unit for determining a cause of the scattered light based on the scattered light detected by the detection unit, wherein the irradiation unit irradiates at least one irradiation light of s-polarization and p-polarization while the detection unit varies a detection angle of the scattered light; and the determination unit determines whether the cause of the scattered light is a foreign material or a microscopic defect based on an amplitude of the detected scattered light. The intensities of the scattered lights form the foreign material and microscopic defect due to the irradiation light of a specific polarization component are varied depending on the respective irradiation angles. Accordingly, by detecting a scattered light at a scattering angle which renders the intensities of the scattered lights from the foreign material and the microscopic defect significantly different, it is possible to appropriately determine whether that on the surface of the object is a foreign material or a microscopic defect.

Preferably, the irradiation unit irradiates an irradiation light of s-polarization at a small irradiation angle while the detection unit detects the scattered light at a small scattering angle, and the determination unit determines that the cause of the scattered light is the foreign material when the detected scattered light has a great amplitude and that the cause of the scattered light is the microscopic defect when the detected scattered light has a small amplitude. As for the small scattering angle, the amplitude of the scattered light from the foreign material due to the s-polarization irradiation light of small irradiation angle is greater than the amplitude of the scattered light from the microscopic defect due to the s-polarization irradiation light of small irradiation angle. Accordingly, it is possible to positively determine whether that on the surface of the object is a foreign material or a microscopic defect.

Preferably, the irradiation unit irradiates an irradiation light of p-polarization at a large irradiation angle while the detection unit detects the scattered light at a large scattering angle, and the determination unit determines that the cause of the scattered light is the microscopic defect when the detected scattered light has a great amplitude and that the cause of the scattered light is the foreign material when the detected scattered light has a small amplitude. As for the large scattering angle, the amplitude of the scattered light from the microscopic defect due to the p-polarization irradiation light of large irradiation angle is greater than the amplitude of the scattered light from the foreign material due to the p-polarization irradiation light of large irradiation angle. Accordingly, it is possible to positively determine whether that on the surface of the object is a foreign material or a microscopic defect.

Preferably, the irradiation unit irradiates irradiation lights of s-polarization and p-polarization while varying irradiation angles thereof, and the determination unit determines that the cause of the scattered light is the foreign material when the amplitude of the scattered light at a small scattering angle due to the irradiation light of s-polarization at a small irradiation angle is great, whereas the determination unit determines that the cause of the scattered light is a microscopic defect when the amplitude of the scattered light at a large scattering angle due to the irradiation light of p-polarization at a large irradiation angle is great. As for the small scattering angle, the amplitude of the scattered light from the foreign material due to the s-polarization irradiation light of small irradiation angle is great, whereas as for the large scattering angle, the amplitude of the scattered light from the microscopic defect due to the p-polarization irradiation light of large irradiation angle is great. Accordingly, it is possible to positively determine whether that on the surface of the object is a foreign material or a microscopic defect.

Preferably, the determination unit determines that the cause of the scattered light is the foreign material when the amplitude of the scattered light due to the irradiation light of s-polarization has a peak value at a scattering angle of 20 degrees or thereabout with respect to the surface of the object and that the cause of the scattered light is a microscopic defect when the amplitude of the scattered light due to the irradiation light of p-polarization has a peak value at a scattering angle of 90 degrees or thereabout with respect to the surface of the object. The amplitude of the scattered light from the foreign material due to the s-polarization irradiation light of the irradiation angle of 20 degrees or thereabout has a peak value at the scattering angle of 20 degrees or thereabout, whereas the amplitude of the scattered light from the microscopic defect due to the p-polarization irradiation light of the irradiation angle of 90 degrees or thereabout has a peak value at the scattering angle of 90 degrees or thereabout. Accordingly, it is possible to positively determine whether that on the surface of the object is a foreign material or a microscopic defect.

In accordance with still another aspect of the present invention, there is provided an apparatus for inspecting a surface of an object to be processed, including: at least one irradiation unit for irradiating a light on the surface of the object; at least one detection unit for detecting a light scattered from the surface of the object in response to the irradiated light; and a determination unit for determining a cause of the scattered light based on the scattered light detected by the detection unit, wherein the irradiation unit irradiates at least one irradiation light of s-polarization and p-polarization; the detection unit is fixed to detect the scattered light at a detection angle; and the determination unit determines whether the cause of the scattered light is a foreign material or a microscopic defect based on an amplitude of the detected scattered light. The amplitudes of the scattered lights form the foreign material and microscopic defect due to the irradiation light of a specific polarization component are varied depending on the respective scattering angles. Accordingly, by setting the detection angle properly, it is possible to appropriately determine whether that on the surface of the object is a foreign material or a microscopic defect without varying the detection angle of the detection unit, thereby simplifying the constructions of the object surface inspection apparatus.

Preferably, the irradiation unit is fixed to irradiate an irradiation light of s-polarization at a small irradiation angle while the detection unit is fixed to detect the scattered light at a small scattering angle, and the determination unit determines that the cause of the scattered light is the foreign material when the detected scattered light has a great amplitude and that the cause of the scattered light is the microscopic defect when the detected scattered light has a small amplitude. As for the small scattering angle, the amplitude of the scattered light from the foreign material due to the s-polarization irradiation light of small irradiation angle is greater than the amplitude of the scattered light from the microscopic defect due to the s-polarization irradiation light of small irradiation angle. Accordingly, it is possible to positively determine whether that on the surface of the object is a foreign material or a microscopic defect.

Preferably, the irradiation unit is fixed to irradiate an irradiation light of p-polarization at a large irradiation angle while the detection unit is fixed to detect the scattered light at a large scattering angle, and the determination unit determines that the cause of the scattered light is the microscopic defect when the detected scattered light has a great amplitude and that the cause of the scattered light is the foreign material when the detected scattered light has a small amplitude. As for the large scattering angle, the amplitude of the scattered light from the microscopic defect due to the p-polarization irradiation light of large irradiation angle is greater than the amplitude of the scattered light from the foreign material due to the p-polarization irradiation light of large irradiation angle. Accordingly, it is possible to positively determine whether that on the surface of the object is a foreign material or a microscopic defect.

Preferably, the irradiation unit irradiate the irradiation light of s-polarization at a small irradiation angle and the irradiation light of p-polarization at a large irradiation angle while the detection unit is fixed to detect the scattered lights at a large and a small scattering angle, respectively, and the determination unit determines that the cause of the scattered light is the foreign material when the scattered light of the small scattering angle due to the irradiation light of s-polarization has a great amplitude, whereas the determination unit determines that the cause of the scattered light is the microscopic defect when the scattered light of the large scattering angle due to the irradiation light of p-polarization has a great amplitude. As for the small scattering angle, the amplitude of the scattered light from the foreign material due to the s-polarization irradiation light of small irradiation angle is great, whereas as for the large scattering angle, the amplitude of the scattered light from the microscopic defect due to the p-polarization irradiation light of large irradiation angle is great. Accordingly, it is possible to positively determine whether that on the surface of the object is a foreign material or a microscopic defect.

BRIEF DESCRIPTION OF THE DRAWINGS

The above and other objects and features of the present invention will become apparent from the following description of preferred embodiments given in conjunction with the accompanying drawings, in which:

FIGS. 1A and 1B show a schematic configuration of an object surface inspection apparatus in accordance with a first preferred embodiment of the present invention, wherein FIGS. 1A and 1B are a side view and a top view thereof, respectively;

FIGS. 2A to 2D illustrate defects on a wafer surface to be inspected by the object surface inspection apparatus in accordance with the first embodiment of the present invention, wherein FIG. 2A is a perspective view of a particle adhered on a wafer surface; FIG. 2B is a cross sectional view taken along the line A-A in FIG. 2A; FIG. 2C is a perspective view of a pinhole formed in a wafer surface; and FIG. 2D is a cross sectional view taken along the line B-B in FIG. 2C;

FIGS. 3A and 3B show schematic views to describe generation of scattered lights when laser beams are irradiated to defects on wafer surfaces, wherein FIG. 3A illustrates a case where a laser beam is irradiated vertically to a particle from above while FIG. 3B describes a case where a laser beam is irradiated vertically to a pinhole from above;

FIGS. 4A and 4B show models for an electromagnetic wave analysis of intensity distributions of scattered lights that are varied depending on a polarization component or an irradiation angle of a laser beam, wherein FIG. 4A is a model for analyzing intensity distributions of scattered lights from a pinhole while FIG. 4B illustrates a model for analyzing intensity distributions of scattered lights from a particle;

FIGS. 5A to 5F describe analysis results of intensity distributions of scattered lights in case of applying a p-polarization component laser beam, wherein FIGS. 5A, 5C and 5E show analysis results for a pinhole in cases where the irradiation angles of the laser beam are set to be 15, 45 and 90 degrees, respectively, while FIGS. 5B, 5D and 5F illustrate analysis results for a particle in cases where the irradiation angles of the laser beam are set to be 15, 45 and 90 degrees, respectively;

FIGS. 6A to 6F describe analysis result of intensity distributions of scattered lights in case of applying an s-polarization component laser beam, wherein FIGS. 6A, 6C and 6E show analysis result for a pinhole in cases where the irradiation angles of the laser beam are set to be 15, 45 and 90 degrees, respectively, while FIGS. 6B, 6D and 6F illustrate analysis result for a particle in cases where the irradiation angles of the laser beam are set to be 15, 45 and 90 degrees, respectively;

DETAILED DESCRIPTION OF THE PREFERRED EMBODIMENTS

Figure 1A:
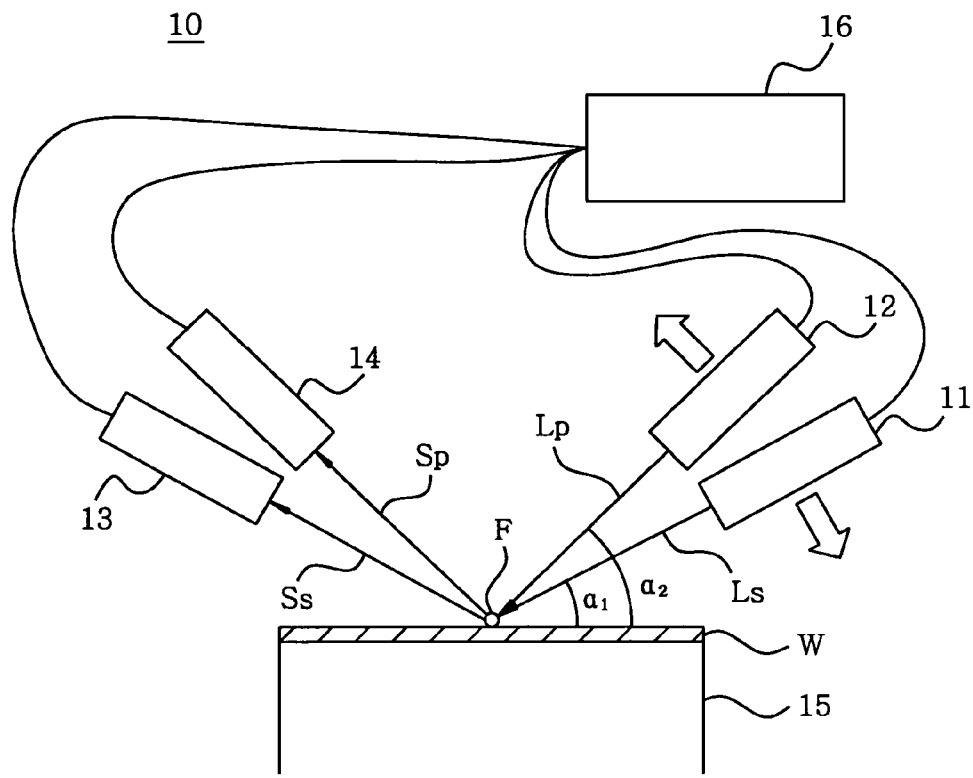

In order to achieve the aforementioned objects, the inventor has researched to find that, in an apparatus for inspecting a surface of an object to be processed (hereinafter, referred to as "object surface inspection apparatus"), which includes at least one irradiation unit for irradiating a light on the surface of the object; at least one detection unit for detecting a light scattered from the surface of the object in response to the irradiated light; and a determination unit for determining a cause of the scattered light based on the scattered light detected by the detection unit, when irradiating at least one irradiation light of s-polarization and p-polarization while varying an irradiation angle of the irradiated light and determining whether the cause of the scattered light is a foreign material or a microscopic defect based on an intensity of the detected scattered light, it is possible to appropriately determine whether that on the surface of the object is a foreign material or a microscopic defect by irradiating an irradiation light at an irradiation angle which renders the intensities of the scattered lights from the foreign material and the microscopic defect significantly different from each other.

The inventor has also found that, in the above object surface inspection apparatus, when irradiating at least one irradiation light of s-polarization and p-polarization while fixing the irradiation unit to irradiate the light at an angle and determining whether the cause of the scattered light is a foreign material or a microscopic defect based on an intensity of the detected scattered light, by setting the irradiation angle properly, it is possible to appropriately determine whether that on the surface of the object is a foreign material or a microscopic defect without varying the irradiation angle of the irradiation light, thereby simplifying the constructions of the object surface inspection apparatus.

Further, the inventor has found that, in the above object surface inspection apparatus, when irradiating at least one irradiation light of s-polarization and p-polarization while varying a detection angle of the scattered light and determining whether the cause of the scattered light is a foreign material or a microscopic defect based on an amplitude of the detected scattered light, by detecting the scattered light at a scattering angle which renders the intensities of the scattered lights from the foreign material and the microscopic defect significantly different from each other, it is possible to appropriately determine whether that on the surface of the object is a foreign material or a microscopic defect.

Furthermore, the inventor has found that, in the above object surface inspection apparatus, when irradiating at least one irradiation light of s-polarization and p-polarization while the detection unit is fixed to detect the scattered light at a detection angle and determining whether the cause of the scattered light is a foreign material or a microscopic defect based on an amplitude of the detected scattered light, by setting the detection angle properly, it is possible to appropriately determine whether that on the surface of the object is a foreign material or a microscopic defect without varying the detection angle of the detection unit, thereby simplifying the constructions of the object surface inspection apparatus.

The present invention has been conceived based on the results of the above research.

Hereinafter, preferred embodiments of the present invention will be described with reference to the accompanying drawings.

First, an apparatus for inspecting a surface of an object to be processed (hereinafter, referred to as "object surface inspection apparatus") in accordance with a first preferred embodiment of the present invention will be described in detail.

Figure 1B:
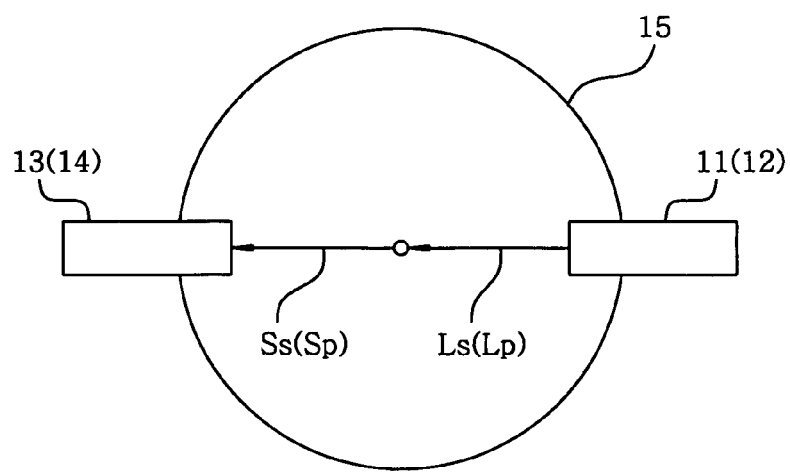

FIGS. 1A and 1B show a schematic configuration of the object surface inspection apparatus in accordance with the first preferred embodiment of the present invention. FIG. 1A is a side view of the apparatus while FIG. 1B is a top view thereof.

In FIG. 1A, a wafer surface inspection apparatus (object surface inspection apparatus) 10 includes two laser beam illuminators (illumination unit) 11 and 12 for irradiating laser beams to an inspection site on a surface of a wafer (object to be processed) W (hereinafter, referred to as a "wafer surface"); two scattered light detectors (detection unit) 13 and 14 for detecting scattered lights generated by the irradiated laser beams; a stage 15 for mounting the wafer W thereon; an operation unit (determination unit) 16 connected to the laser beam illuminators 11 and 12 and the scattered light detectors 13 and 14; and an air filter (not shown) for purifying the air within the wafer surface inspection apparatus 10, particularly, the air around the stage 15.

The two laser beam illuminators 11 and 12 irradiate, for example, semiconductor laser beams or carbon dioxide laser beams to a wafer surface at elevation angles (hereinafter, referred to as "irradiation angles") $\alpha_1$ and $\alpha_2$ with respect to the wafer surface, respectively. In the first embodiment of the present invention, the laser beam illuminator 11 irradiates an s-polarized laser beam Ls while the laser beam illuminator 12 irradiates a p-polarized laser beam Lp. Further, the laser beam illuminators 11 and 12 are configured to be movable in directions marked by arrows in FIG. 1A. That is, the irradiation angles can be varied, and, also, the intensity of the irradiated laser beams can be adjusted as well.

Each of the two scattered light detectors 13 and 14 is formed of, e.g., a photomultiplier tube (PMT) or a charge coupled device (CCD). When a defect F, e.g., a particle (foreign material) adhered on a resist film or a pinhole (microscopic defect) such as an air bubble in the resist, exists at an inspection site on the wafer surface, the scattered light detectors 13 and 14 detect scattered lights generated from the defect F by the irradiated laser beams and transmit detection signals to the operation unit 16 based on the detected scattered lights. In the first embodiment, the scattered light detector 13 detects a scattered light Ss generated by the laser beam Ls while the scattered light detector 14 detects a scattered light Sp generated by the laser beam Lp. Also, the detection sensibilities of the scattered light detectors 13 and 14 can be controlled appropriately.

The stage 15 is a mounting table with a columnar shape, and it is rotatable about a central axis and also movable both horizontally and vertically. The laser beams Lp and Ls are irradiated to a desired inspection site on the surface of the wafer W loaded on the mounting table.

The operation unit 16 has a CPU for determining whether a cause of the scattered lights is a particle or a pinhole, i.e., whether the scattered lights are generated due to a particle or a pinhole based on the detection signals transmitted from the scattered light detectors 13 and 14 and controlling the irradiation timing, the irradiation angle and/or the intensity of laser beams of the laser beam illuminator 11 and 12.

The wafer surface inspection apparatus 10 is installed in a plasma system, e.g., in an etching processing system to inspect some or all of wafers in the course of manufacturing semiconductor devices.

Figure 2A:
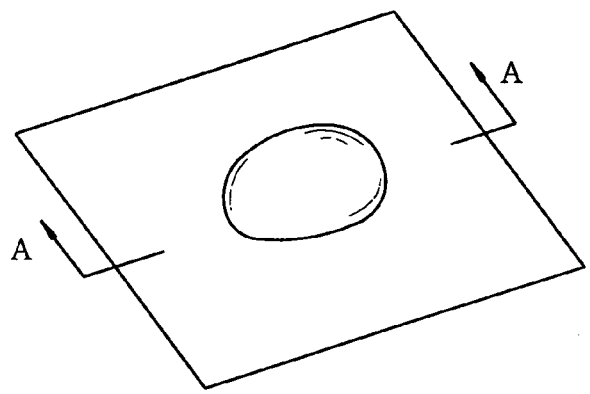
Figure 2B:
Figure 2C:
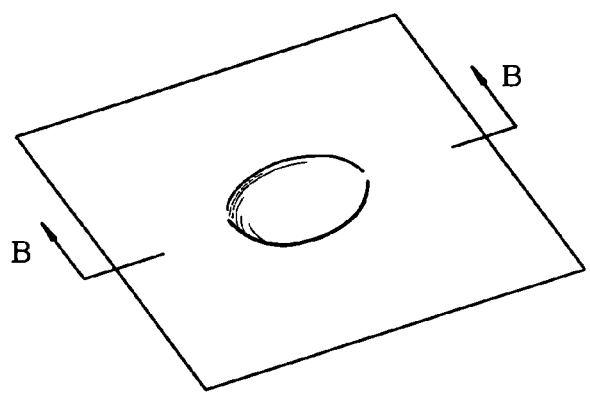
Figure 2D:

FIGS. 2A to 2D present schematic views to illustrate defects on wafer surfaces to be inspected by the object surface inspection apparatus in accordance with the first embodiment of the present invention. FIG. 2A is a perspective view of a particle adhered on a wafer surface; FIG. 2B sets forth a cross sectional view taken along the line A-A in FIG. 2A; FIG. 3 provides a perspective view of a pinhole in a resist formed on a wafer surface; and FIG. 2D shows a cross sectional view taken along the line B-B in FIG. 2C.

In processing chambers or transfer chambers of a plasma processing system, there exist particles that are introduced thereinto from the outside of the system. Accordingly, when performing a plasma processing on a wafer in each chamber or when transferring a wafer in each transfer chamber, particles can be adhered to the wafer. In recent fine semiconductor devices, the size of a particle that might cause a problem is about 100 nm. If a particle of that size adheres to the surface of the wafer, it causes a convex defect on the wafer surface, as illustrated in FIGS. 2A and 2B.

In case of performing a plasma processing, for example, an etching processing on a wafer, a resist film with a thickness of, e.g., 2000 Å (200 nm) is formed on the surface of the wafer. However, if an air bubble is generated in the resist film or if an impact is exerted on the wafer after the formation of the resist film, the resist film may have partial cutout portions. The partial cutout portions in the resist film (hereinafter, referred to as "pinhole") cause a concave defect on the wafer surface, as illustrated in FIGS. 2C and 2D. Such a concave defect has an width of about 100 nm and a depth of about 2000 Å (200 nm). That is, the concave defect has a depth substantially identical to or greater than its width. Further, such concave defect is also caused in a silicon oxide ($SiO_2$) film or a silicon nitride (SiN) film as well as the resist film.

Figure 3A:
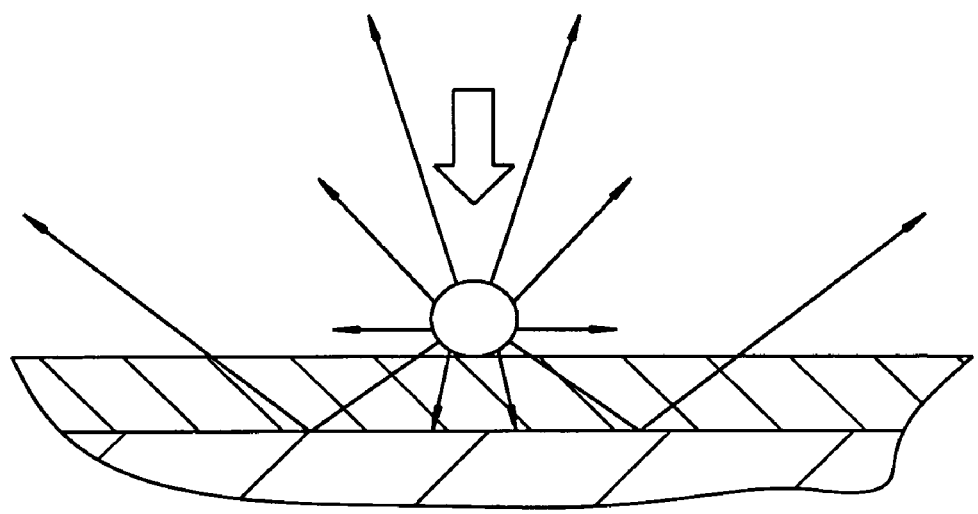
Figure 3B:
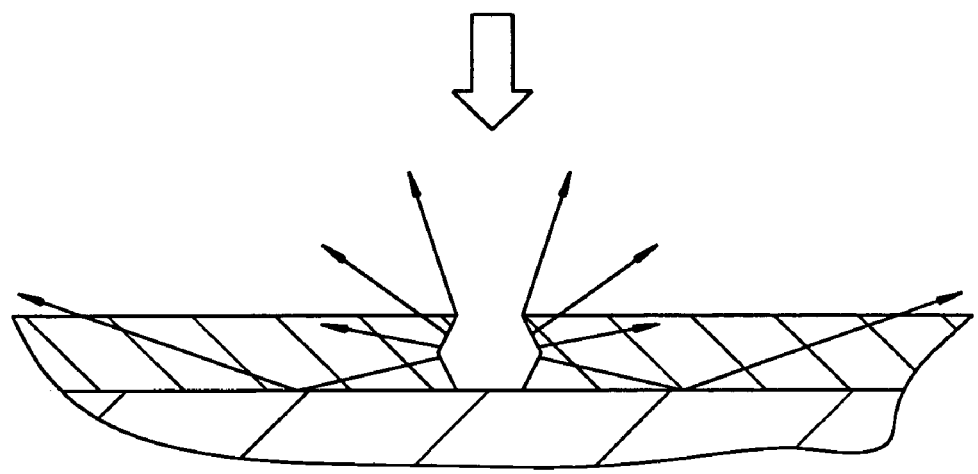

FIGS. 3A and 3B show schematic views to describe generation of scattered lights when laser beams are irradiated to defects on wafer surfaces. FIG. 3A illustrates a case where a laser beam is irradiated vertically to a particle from above while FIG. 3B describes a case where a laser beam is irradiated vertically to a pinhole from above.

It has been known that Mie scattering occurs when a laser beam is irradiated to a globular particle with a wavelength substantially identical to the size of the particle. Here, since laser beams from the laser beam illuminators 11 and 12 typically have a wavelength of about 488 nm and the size of the particle is about 100 nm as mentioned before, the lights are scattered according to an Mie scattering theory when the laser beams are irradiated to the particle as shown in FIGS. 2A and 2B. To be specific, as shown in FIG. 3A, not only a backscattering (backward scattering) toward a direction opposite to a direction in which a laser beam is irradiated but also a peripheral scattering in directions other than the direction opposite to the laser beam irradiation direction (hereinafter, referred to as "peripheral directions") occurs. As shown in FIG. 3A, the intensities of scattered lights of the backscattering are greater than those of the peripheral scattering. The intensities of the scattered lights in the peripheral directions are small and, particularly, scattered lights generated in directions downward from the particle are extinguished as they arrive at the wafer after penetrating the resist film or they are scattered through the resist film again after being reflected by the wafer surface. That is, since the intensities of scattered lights vary depending on scattering directions, the intensities of the scattered lights from the particle depend on their scattering angles.

Meanwhile, if a laser beam is irradiated to the pinhole as shown in FIGS. 2C and 2D, the laser beam is refracted due to a difference in refractive index at an interface between the atmosphere and the resist. As for the pinhole, since the interface between the atmosphere and the resist is not oriented in a single direction, the irradiated laser beam would be refracted in all directions, as shown in FIG. 3B. That is, since the laser beam is refracted not only in a direction opposite to the laser beam irradiation direction but also in peripheral directions, the refracted laser beams scatter substantially as scattered lights. Since the intensities of those scattered lights vary depending on their scattering directions, the intensities of the scattered lights from the pinhole are dependent on their scattering angles.

Here, the configurations of the scattered lights from the pinhole are different from those from the particle, as shown in FIGS. 3A and 3B. Therefore, it is possible to distinguish the particle and the pinhole by using the difference in the configurations of the scattered lights. That is, the particle and the pinhole can be distinguished based on the intensities of the detected scattered lights.

Moreover, since the particle and the pinhole have different shapes, the scattered lights from the particle and the pinhole have different intensity distributions depending on a polarization component or an irradiation angle of a laser beam, as will be described below.

Figure 4A:
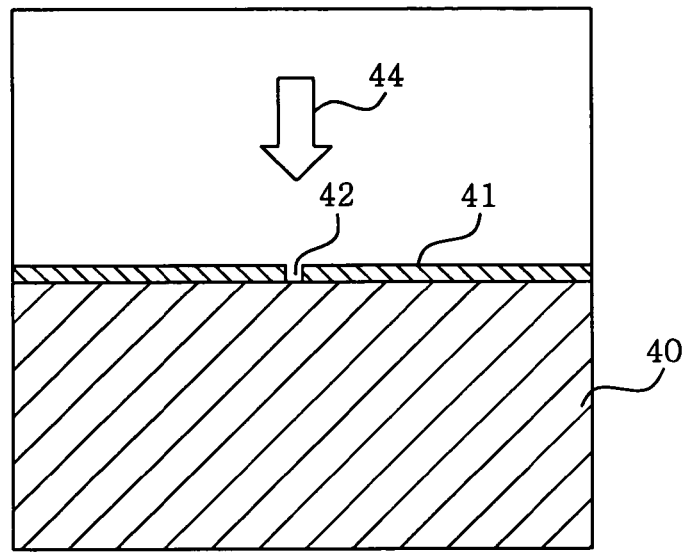
Figure 4B:
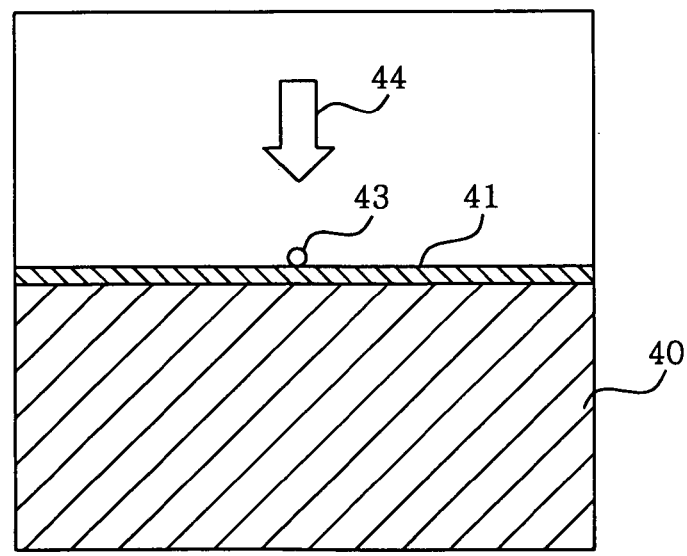

FIGS. 4A and 4B show models for an electromagnetic wave analysis of an intensity distribution of scattered lights that is varied depending on a polarization component or an irradiation angle of a laser beam. FIGS. 4A and 4B are models for analyzing intensity distributions of scattered lights from a pinhole and a particle, respectively.

In the model for the electromagnetic analysis of a pinhole shown in FIG. 4A, the pinhole is implemented by forming a partial cutout portion 42 in a resist film model 41 deposited on a wafer model 40. In the model for the electromagnetic analysis of a particle shown in FIG. 4B, the particle is implemented by disposing a globular particle model 43 on the top surface of a resist film model 41. Further, since the models for the electromagnetic wave analysis of the pinhole and the particle are configured such that the wafer model 40 and the resist film model 41 can be inclined at desired angles with respect to a laser beam 44 irradiated vertically from above, the irradiation angle of the laser beam 44 can be changed by using these electromagnetic wave models. Also, the polarization component of the laser beam 44 can be set to be a p-polarization or an s-polarization.

An analysis of an intensity distribution of scattered lights was conducted by setting the polarization component of the laser beam 44 as a p-polarization or an s-polarization, setting the irradiation angle of the laser beam as 15, 45 or 90 degrees and solving a Maxwell equation with a finite-difference time-domain (FD-TD) method by using the above-described electromagnetic wave analysis models. Parameters for the analysis are as follows.

Surface dimension of wafer model 40: 10 µm×10 µm
Mesh number of resist film model 41: 256×256×1
Wavelength and energy of laser beam 44: 488 nm, 1 mW/cm$^2$
Opening size of partial cutout portion 42: $\phi$=100 nm
Size of globular particle model 43: $\phi$=100 nm
Thickness of resist film model 41: 2000 Å (200 nm)
Refractive index of the atmosphere: 1.00+0.07i
Refractive index of resist film model 41: 1.46+0.0003i
Refractive index of wafer model 40: 3.85+0.01i First, analysis results of an intensity distribution of scattered lights will be described for the case where the polarization component of the laser beam 44 is set as a p-polarization.

Figure 5A:
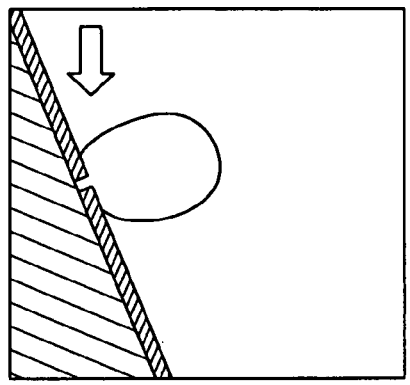
Figure 5B:
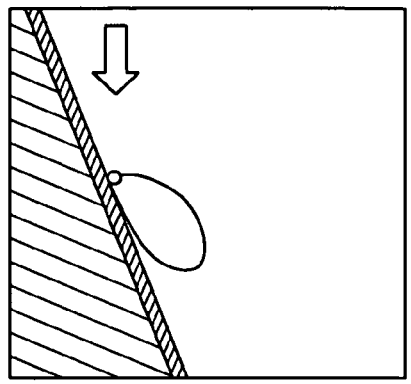
Figure 5C:
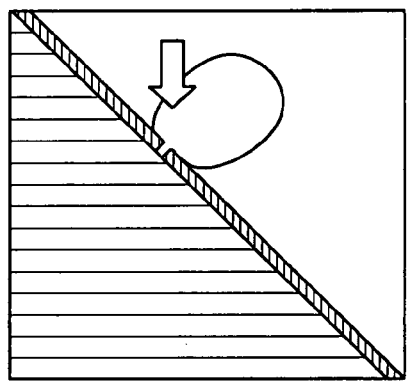
Figure 5D:
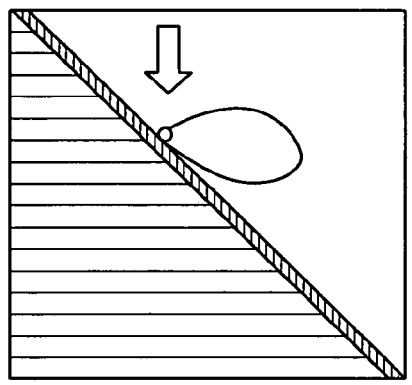
Figure 5E:
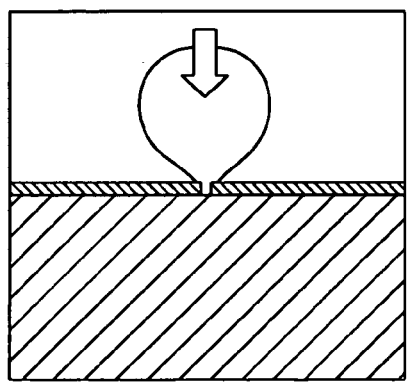
Figure 5F:
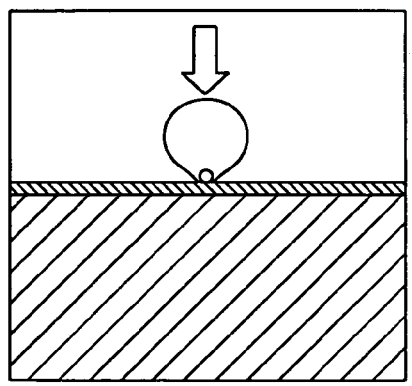

FIGS. 5A to 5F describe analysis results of the intensity distribution of scattered lights in the case where a p-polarized laser beam is irradiated. FIGS. 5A, 5C and 5E show the analysis results for a pinhole in cases where the irradiation angles of the laser beam are set to be 15, 45 and 90 degrees, respectively, while FIGS. 5B, 5D and 5F illustrate the analysis result for a particle in cases where the irradiation angles of the laser beam are set to be 15, 45 and 90 degrees, respectively.

In the case where the irradiation angle of the laser beam is set to be 15 degrees, the amount of scattered lights generated in an upward direction normal to the surface of the wafer model 40 from the pinhole is great as shown in FIG. 5A, whereas the amount of scattered lights generated in an irradiation direction of the laser beam 44 (hereinafter, referred to as "forward direction") from the particle is great as shown in FIG. 5B.

Further, in the case where the irradiation angle of the laser beam is set to be 45 degrees, the amount of scattered lights generated in the upward direction normal to the surface of the wafer model 40 from the pinhole is great shown in FIG. 5C, whereas the amount of scattered lights generated in the forward direction from the particle is great as shown in FIG. 5D.

Also, in the case where the irradiation angle of the laser beam is set to be 90 degrees, the amount of scattered lights generated in the upward direction from the pinhole is great as shown in FIG. 5E. Meanwhile, as for the particle, although scattered lights are generated in the upward direction as shown in FIG. 5F, their intensities are smaller than those of the scattered lights from the pinhole.

Next, an analysis result of an intensity distribution of scattered lights will be described for the case where the polarization component of the laser beam 44 is set as an s-polarization.

Figure 6A:
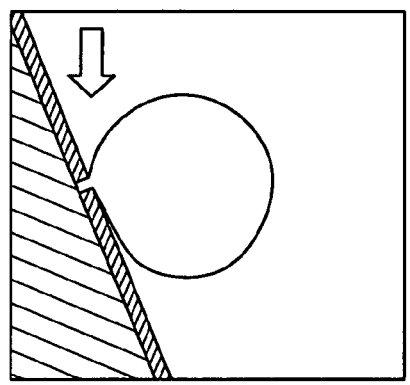
Figure 6B:
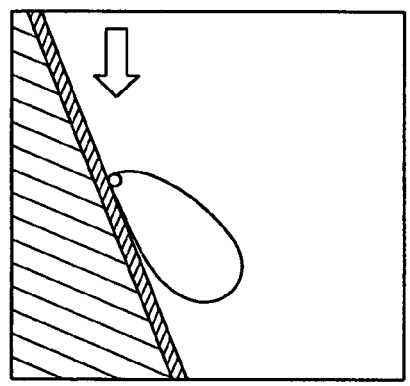
Figure 6C:
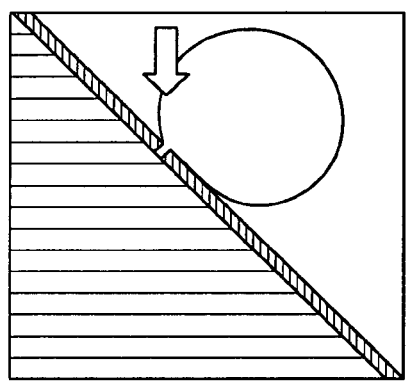
Figure 6D:
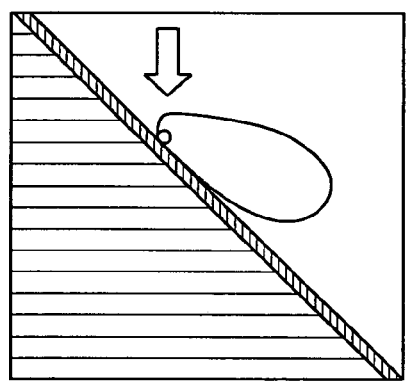
Figure 6E:
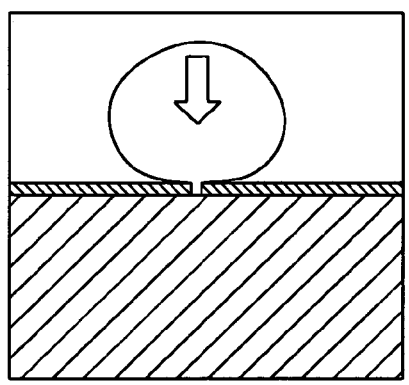
Figure 6F:
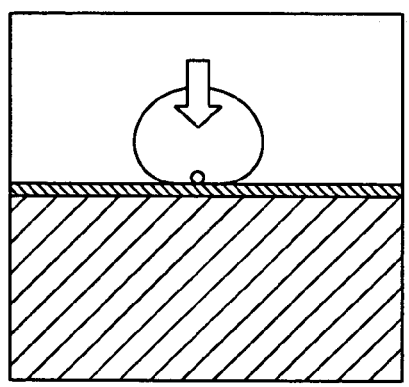

FIGS. 6A to 6F show analysis results of the intensity distribution of scattered lights in cases where the s-polarization component laser beam is irradiated. FIGS. 6A, 6C and 6E show the analysis results for a pinhole in cases where irradiation angles of the laser beam are set to be 15, 45 and 90 degrees, respectively, while FIGS. 6B, 6D and 6F illustrate the analysis result for a particle in cases where irradiation angles of the laser beam are set to be 15, 45 and 90 degrees, respectively.

In the case where the irradiation angle of the laser beam is set to be 15 degrees, the amount of scattered lights generated in the upward direction from the pinhole is great as shown in FIG. 6A, whereas, as for the particle, the amount of scattered lights generated in the forward direction is great as shown in FIG. 6B. Moreover, in comparison with the p-polarization case (FIGS. 5A and 5B), the intensities of the scattered lights from both the pinhole and the particle are greater in the case of the s-polarization. Particularly, the amount of the scattered lights generated from the pinhole in peripheral directions is greater in case of the s-polarized laser beam than in case of the p-polarized laser beam.

In case the irradiation angle of the laser beam is set to be 45 degrees, the amount of scattered lights generated in the upward direction from the pinhole is great as shown in FIG. 6C, whereas the amount of scattered lights generated in the forward direction from the particle is great as shown in FIG. 6D. Further, in comparison with the p-polarization case (FIGS. 5C and 5D), the intensities of the scattered lights from both the pinhole and the particle are greater in the case of the s-polarization. Particularly, the amount of the scattered lights generated from the pinhole in peripheral directions is greater in case of the s-polarized laser beam than in case of the p-polarized laser beam.

Also, in case the irradiation angle of the laser beam is set to be 90 degrees, the amount of scattered lights generated in the upward direction from the pinhole is great as shown in FIG. 6E. Meanwhile, as for the particle, although scattered lights are generated in the upward direction as shown in FIG. 6F, their intensities are smaller than the intensities of scattered lights from the pinhole. Furthermore, when compared with the p-polarization cases (FIGS. 5E and 5F), the amount of the scattered lights generated from the pinhole and the particle in peripheral directions is greater in case of the s-polarization than in case of the p-polarization.

As described above, scattered lights from the particle and the pinhole exhibit different distributions in their intensities depending on the polarization component or the irradiation angle of the laser beam irradiated thereto. Accordingly, through a series of steps including irradiating laser beams Ls and Lp to a defect on a wafer surface at different irradiation angles $\alpha_1$ and $\alpha_2$, respectively, by way of moving the laser beam illuminators 11 and 12 of the wafer surface inspection apparatus 10; detecting the intensities of scattered lights Ss and Sp, which are generated by the respective irradiated laser beams Ls and Lp, by using the scattered light detectors 13 and 14; and analyzing the intensities of the detected scattered lights Ss and Sp, it becomes possible to determine whether the defect on the wafer surface is a particle or a pinhole.

With the object surface inspection apparatus in accordance with the first embodiment of the present invention, laser beams Ls and Lp are irradiated to an inspection site on a wafer surface at different irradiation angles $\alpha_1$ and $\alpha_2$, respectively, and the cause of scattered lights Ss and Sp generated by the laser beams Ls and Lp are determined based on the intensities of the scattered lights Ss and Sp. The intensities of the scattered lights from a particle and a pinhole are varied depending on the irradiation angles of the laser beams Ls and Lp. Accordingly, by irradiating the laser beams Ls and Lp at irradiation angles that make the intensities of the scattered lights from the particle and the pinhole significantly different from each other, it becomes possible to determine whether a defect F on the wafer surface is a particle or a pinhole.

Moreover, since it is possible to determine whether the defect F on the wafer surface is a particle or a pinhole, there is no case of erroneously determining that a particle is attached on the wafer surface. Accordingly, an unnecessary cleaning of a manufacturing line and a dummy running after the cleaning operation can be avoided, which prevents a deterioration in an operating rate of the manufacturing line. Also, the cause of the defect can be specified accurately.

Further, as shown in FIGS. 5A to 6F, scattered lights from a particle and a pinhole show different intensity distributions even though laser beams with a same polarization component are irradiated thereto. Thus, by irradiating laser beams with a single polarization component, it is possible to determine whether scattered lights are generated due to a particle or a pinhole. That is to say, the wafer surface inspection apparatus 10 can determine whether a defect F on a wafer surface is a particle or a pinhole by using any one of the laser beam illuminators 11 and 12. At this time, the wafer surface inspection apparatus 10 may include either the scattered light detector 13 or 14.

In addition, as shown in FIGS. 5A to 6F, scattered lights from a particle and a pinhole show different intensity distributions even though laser beams are irradiated at a same irradiation angle. Thus, by irradiating laser beams at a same irradiation angle, it is possible to determine whether scattered lights are generated due to a particle or a pinhole. That is, the laser beam illuminators 11 and 12 may irradiate laser beams Ls and Lp at a same irradiation angle.

Further, by fixing the laser beam illuminators 11 and 12 such that they irradiate laser beams Ls and Lp at irradiation angles which make the intensities of scattered lights from a particle and a pinhole significantly different from each other, it is possible to determine whether a defect F on a wafer surface is a particle or a pinhole, and also to simplify configuration of the wafer surface inspection apparatus 10. Here, since the laser beam illuminators 11 and 12 need not be moved, generation of particles due to the movement can be prevented.

Hereinafter, an object surface inspection apparatus in accordance with a second preferred embodiment of the present invention will be described in detail.

Figure 7:
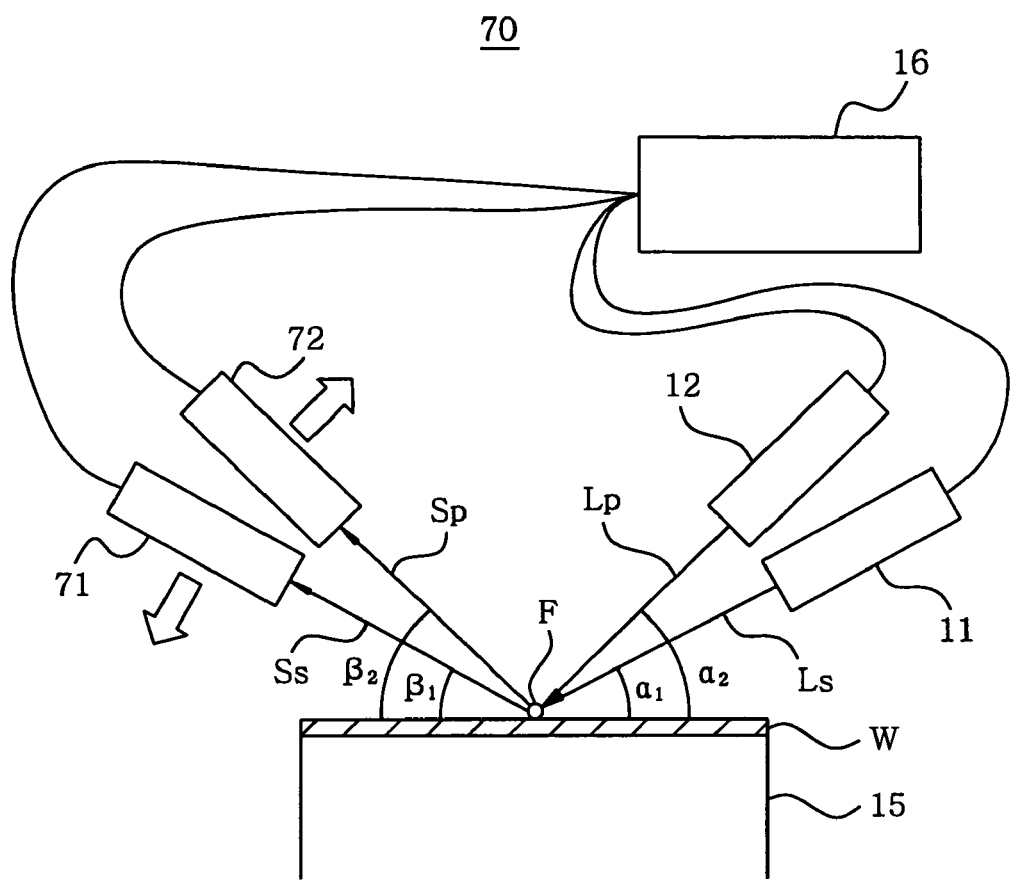
FIG. 7 presents a side view to show a schematic configuration of an object surface inspection apparatus in accordance with a second preferred embodiment of the present invention.

FIG. 7 presents a side view to illustrate a schematic configuration of the object surface inspection apparatus in accordance with the second embodiment of the present invention.

Since the configuration and the function of the second embodiment is basically identical with those of the first embodiment described above, descriptions on like parts and functions will be omitted; and instead distinctive parts and functions will be focused and elaborated.

In FIG. 7, a wafer surface inspection apparatus 70 includes two scattered light detectors 71 and 72 for detecting scattered lights generated by the irradiation of laser beams. In the second embodiment, the scattered light detector 71 detects a scattered light Ss generated by a laser beam Ls at a detection angle $\beta_1$ while the scattered light detector 72 detects a scattered light Sp generated by a laser beam Lp at a detection angle $\beta_2$. Further, the scattered light detectors 71 and 72 are configured such that they are movable in directions marked by arrows in FIG. 7 in order to vary their detection angles $\beta_1$ and $\beta_2$, respectively.

Here, as described before, the intensities of scattered lights from a particle and a pinhole vary depending on scattering angles, and the configurations of the scattered lights from the particle and the pinhole are different from each other. That is, the intensity distributions of the scattered lights from the particle and the pinhole are different from each other. Accordingly, the wafer surface inspection apparatus 70 can determine whether a defect F on a wafer surface is a particle or a pinhole by irradiating laser beams Ls and Lp thereto from the laser beam illuminators 11 and 12, respectively, detecting scattered lights Ss and Sp generated due to the laser beams Ls and Lp by using the scattered light detectors 71, 72 while varying detection angles $\beta_1$ and $\beta_2$, and then analyzing the intensity distributions of the detected scattered lights Ss and Sp.

With the object surface inspection apparatus in accordance with the second embodiment of the present invention, laser beams Ls and Lp are irradiated to an inspection site on a wafer surface, and scattered lights Ss and Sp generated due to the laser beams Ls and Lp are detected by the scattered light detectors 71 and 72 while detection angles $\beta_1$ and $\beta_2$ are varied. Then, the cause of the scattered lights is determined based on the intensity distributions of the scattered lights Ss and Sp. The intensities of the scattered lights Ss and Sp generated by the irradiation of laser beams Ls and Lp to a particle or a pinhole vary depending on scattering angles, respectively, and the scattered lights from the particle and the pinhole have different intensity distributions. Thus, by detecting respective scattered lights Ss and Sp at scattering angles which make the intensities of the scattered lights from a particle and a pinhole significantly different from each other, it becomes possible to determine whether a defect F on a wafer surface is a particle or a pinhole.

Further, as shown in FIGS. 5A to 6F, scattered lights from a particle and a pinhole show different intensity distributions even though their scattering angles are same. Thus, by detecting a scattered light at a certain scattering angle, it is possible to determine whether the scattered light is generated due to a particle or a pinhole. That is to say, the wafer surface inspection apparatus 10 can determine whether a defect F on a wafer surface is a particle or a pinhole by using any one of scattered light detectors 71 and 72. At this time, the wafer surface inspection apparatus 10 may include either the laser beam illuminator 11 or 12.

Further, by fixing the scattered light detectors 71 and 72 such that they detect the scattered lights Ss and Sp at scattering angles which make the intensities of scattered lights from a particle and a pinhole significantly different from each other, it is possible to determine whether a defect F on a wafer surface is a particle or a pinhole, and also to simplify the configuration of the wafer surface inspection apparatus 10. Here, since the scattered light detectors 71 and 72 need not be moved, generation of particles due to the movement can be prevented.

Moreover, though the object surface inspection apparatuses in accordance with the first and the second embodiment of the present invention have been described to detect a pinhole in a resist film, they can also detect a pinhole in a silicon oxide film or a silicon nitride film. Further, the apparatuses can determine a defect on a thin film with a refractive index greatly different from that of a resist or a defect on a substrate with a refractive index greatly different from that of silicon.

Further, though the object surface inspection apparatuses in accordance with the first and the second embodiment of the present invention have been described to determine a defect F on a wafer surface based on the intensities of scattered lights, the determination of the defect F can also be performed based on the amplitudes of the scattered lights.

Hereinafter, specific examples of the present invention will be described.

EXAMPLE 1

First, a variation in the intensities of scattered lights was detected by using electromagnetic wave analysis models for a pinhole and a particle shown in FIGS. 4A and 4B, respectively, while varying an irradiation angle of a laser beam 44 from 5 degrees to 90 degrees. Parameters used for this analysis were identical with those described before for the analysis of the intensity distribution of scattered lights. The analysis results were provided in a graph in FIG. 8, wherein "intensity of scattered light" represents a sum of intensities of scattered lights over the entire range of scattering angles.

Figure 8:
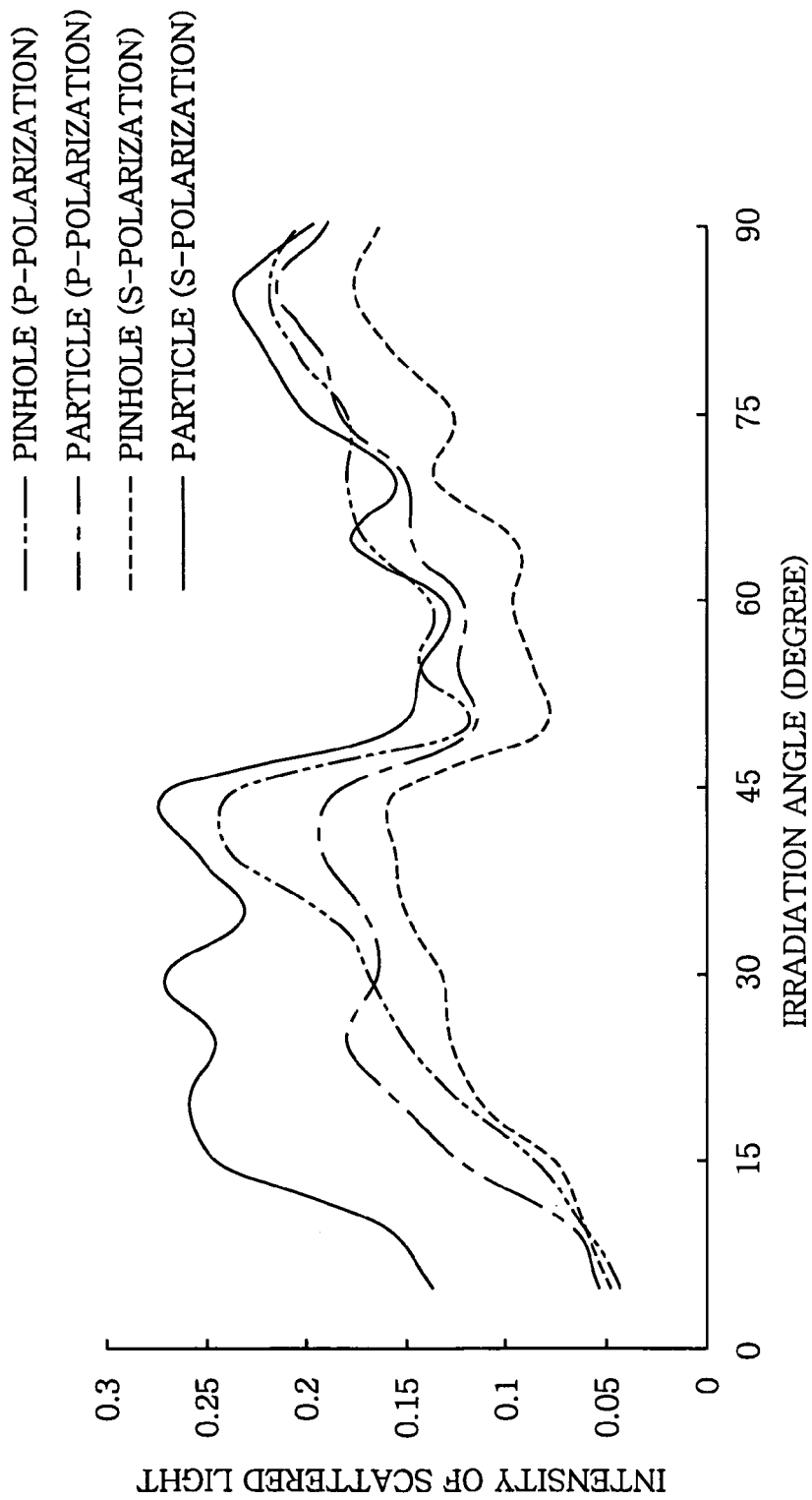
FIG. 8 provides a graph to describe variations in the intensity of scattered lights when the irradiation angle of a laser beam is varied.

In FIG. 8, a solid line represents the intensities of scattered lights from a particle when an s-polarized laser beam is irradiated; a dotted line represents the intensities of scattered lights from a pinhole when an s-polarized laser beam is irradiated; a dashed dotted line represents the intensities of scattered lights from the particle when a p-polarized laser beam is irradiated; and a dashed double-dotted line represents the intensities of scattered lights from the pinhole when a p-polarized laser beam is irradiated.

As can be seen from the graph in FIG. 8, the intensities of the scattered lights from the particle, were greater than those from the pinhole at small irradiation angles when an s-polarized laser beam was applied. That is, the graph indicates that if the intensity of a scattered light generated by an s-polarized laser beam is great at a small irradiation angle, a defect on a wafer surface can be determined as a particle; otherwise, it can be determined as a pinhole.

Specifically, a first s-polarization irradiation beam was applied to a defect on a wafer surface at an irradiation angle of 60 degrees or thereabout (ranging from 45 to 75 degrees) and, at the same time, a second s-polarization irradiation beam was applied to the defect by varying its irradiation angle within a relatively small irradiation angle range of 15 to 45 degrees with respect to the wafer surface. When the defect on the wafer surface was a particle, a ratio of an intensity b1 of a second scattered light generated by the second laser beam to an intensity a1 of a first scattered light generated by the first laser beam (b1/a1) was great; and when the defect was a pinhole, the ratio b1/a1 was small.

The variations of the ratio b1/a1 were provided in Tables 1 to 7. Here, Tables 1 to 7 show variations of the ratio b1/a1 in cases where the irradiation angle of the first irradiation beam (hereinafter, simply referred to as "first irradiation angle") was set to be 45, 50, 55, 60, 65, 70 and 75 degrees, respectively.

TABLE 1

| | First scattered light | | Second scattered light | | |
|---|---|---|---|---|---|
| | Irradiation Angle (Degree) | Intensity: a1 | Irradiation Angle (Degree) | Intensity: b1 | Ratio (b1/a1) |
| Pinhole (s-polarization) | 45 | 0.153 | 15 | 0.074 | 0.483 |
| | | | 20 | 0.112 | 0.732 |
| | | | 25 | 0.127 | 0.830 |
| | | | 30 | 0.131 | 0.856 |

TABLE 1-continued

|  | First scattered light | | Second scattered light | | |
|---|---|---|---|---|---|
|  | Irradiation Angle (Degree) | Intensity: a1 | Irradiation Angle (Degree) | Intensity: b1 | Ratio (b1/a1) |
|  |  |  | 35 | 0.149 | 0.974 |
|  |  |  | 40 | 0.155 | 1.013 |
|  |  |  | 45 | 0.153 | 1.000 |
| Particle (s-polarization) | 45 | 0.270 | 15 | 0.242 | 0.896 |
|  |  |  | 20 | 0.259 | 0.959 |
|  |  |  | 25 | 0.246 | 0.911 |
|  |  |  | 30 | 0.271 | 1.004 |
|  |  |  | 35 | 0.231 | 0.856 |
|  |  |  | 40 | 0.255 | 0.944 |
|  |  |  | 45 | 0.270 | 1.000 |

TABLE 2

|  | First scattered light | | Second scattered light | | |
|---|---|---|---|---|---|
|  | Irradiation Angle (Degree) | Intensity: a1 | Irradiation Angle (Degree) | Intensity: b1 | Ratio (b1/a1) |
| Pinhole (s-polarization) | 50 | 0.082 | 15 | 0.074 | 0.898 |
|  |  |  | 20 | 0.112 | 1.361 |
|  |  |  | 25 | 0.127 | 1.543 |
|  |  |  | 30 | 0.131 | 1.592 |
|  |  |  | 35 | 0.149 | 1.810 |
|  |  |  | 40 | 0.155 | 1.883 |
|  |  |  | 45 | 0.153 | 1.859 |
| Particle (s-polarization) | 50 | 0.158 | 15 | 0.242 | 1.532 |
|  |  |  | 20 | 0.259 | 1.639 |
|  |  |  | 25 | 0.246 | 1.557 |
|  |  |  | 30 | 0.271 | 1.715 |
|  |  |  | 35 | 0.231 | 1.462 |
|  |  |  | 40 | 0.255 | 1.614 |
|  |  |  | 45 | 0.270 | 1.709 |

TABLE 3

|  | First scattered light | | Second scattered light | | |
|---|---|---|---|---|---|
|  | Irradiation Angle (Degree) | Intensity: a1 | Irradiation Angle (Degree) | Intensity: b1 | Ratio (b1/a1) |
| Pinhole (s-polarization) | 55 | 0.086 | 15 | 0.074 | 0.862 |
|  |  |  | 20 | 0.112 | 1.307 |
|  |  |  | 25 | 0.127 | 1.482 |
|  |  |  | 30 | 0.131 | 1.529 |
|  |  |  | 35 | 0.149 | 1.739 |
|  |  |  | 40 | 0.155 | 1.809 |
|  |  |  | 45 | 0.153 | 1.785 |
| Particle (s-polarization) | 55 | 0.142 | 15 | 0.242 | 1.704 |
|  |  |  | 20 | 0.259 | 1.824 |
|  |  |  | 25 | 0.246 | 1.732 |
|  |  |  | 30 | 0.271 | 1.908 |
|  |  |  | 35 | 0.231 | 1.627 |
|  |  |  | 40 | 0.255 | 1.796 |
|  |  |  | 45 | 0.270 | 1.901 |

TABLE 4

|  | First scattered light | | Second scattered light | | |
|---|---|---|---|---|---|
|  | Irradiation Angle (Degree) | Intensity: a1 | Irradiation Angle (Degree) | Intensity: b1 | Ratio (b1/a1) |
| Pinhole (s-polarization) | 60 | 0.097 | 15 | 0.074 | 0.765 |
|  |  |  | 20 | 0.112 | 1.159 |

TABLE 4-continued

|  | First scattered light | | Second scattered light | | |
|---|---|---|---|---|---|
|  | Irradiation Angle (Degree) | Intensity: a1 | Irradiation Angle (Degree) | Intensity: b1 | Ratio (b1/a1) |
|  |  |  | 25 | 0.127 | 1.315 |
|  |  |  | 30 | 0.131 | 1.356 |
|  |  |  | 35 | 0.149 | 1.542 |
|  |  |  | 40 | 0.155 | 1.605 |
|  |  |  | 45 | 0.153 | 1.584 |
| Particle (s-polarization) | 60 | 0.129 | 15 | 0.242 | 1.876 |
|  |  |  | 20 | 0.259 | 2.008 |
|  |  |  | 25 | 0.246 | 1.907 |
|  |  |  | 30 | 0.271 | 2.101 |
|  |  |  | 35 | 0.231 | 1.791 |
|  |  |  | 40 | 0.255 | 1.977 |
|  |  |  | 45 | 0.270 | 2.093 |

TABLE 5

|  | First scattered light | | Second scattered light | | |
|---|---|---|---|---|---|
|  | Irradiation Angle (Degree) | Intensity: a1 | Irradiation Angle (Degree) | Intensity: b1 | Ratio (b1/a1) |
| Pinhole (s-polarization) | 65 | 0.095 | 15 | 0.074 | 0.778 |
|  |  |  | 20 | 0.112 | 1.179 |
|  |  |  | 25 | 0.127 | 1.337 |
|  |  |  | 30 | 0.131 | 1.379 |
|  |  |  | 35 | 0.149 | 1.568 |
|  |  |  | 40 | 0.155 | 1.632 |
|  |  |  | 45 | 0.153 | 1.611 |
| Particle (s-polarization) | 65 | 0.177 | 15 | 0.242 | 1.367 |
|  |  |  | 20 | 0.259 | 1.463 |
|  |  |  | 25 | 0.246 | 1.390 |
|  |  |  | 30 | 0.271 | 1.531 |
|  |  |  | 35 | 0.231 | 1.305 |
|  |  |  | 40 | 0.255 | 1.441 |
|  |  |  | 45 | 0.270 | 1.525 |

TABLE 6

|  | First scattered light | | Second scattered light | | |
|---|---|---|---|---|---|
|  | Irradiation Angle (Degree) | Intensity: a1 | Irradiation Angle (Degree) | Intensity: b1 | Ratio (b1/a1) |
| Pinhole (s-polarization) | 70 | 0.136 | 15 | 0.074 | 0.543 |
|  |  |  | 20 | 0.112 | 0.824 |
|  |  |  | 25 | 0.127 | 0.934 |
|  |  |  | 30 | 0.131 | 0.963 |
|  |  |  | 35 | 0.149 | 1.096 |
|  |  |  | 40 | 0.155 | 1.140 |
|  |  |  | 45 | 0.153 | 1.125 |
| Particle (s-polarization) | 70 | 0.155 | 15 | 0.242 | 1.561 |
|  |  |  | 20 | 0.259 | 1.671 |
|  |  |  | 25 | 0.246 | 1.587 |
|  |  |  | 30 | 0.271 | 1.748 |
|  |  |  | 35 | 0.231 | 1.490 |
|  |  |  | 40 | 0.255 | 1.645 |
|  |  |  | 45 | 0.270 | 1.742 |

TABLE 7

| | First scattered light | | Second scattered light | | |
| --- | --- | --- | --- | --- | --- |
| | Irradiation Angle (Degree) | Intensity: a1 | Irradiation Angle (Degree) | Intensity: b1 | Ratio (b1/a1) |
| Pinhole (s-polarization) | 75 | 0.126 | 15 | 0.074 | 0.587 |
| | | | 20 | 0.112 | 0.889 |
| | | | 25 | 0.127 | 1.008 |
| | | | 30 | 0.131 | 1.040 |
| | | | 35 | 0.149 | 1.183 |
| | | | 40 | 0.155 | 1.230 |
| | | | 45 | 0.153 | 1.214 |
| Particle (s-polarization) | 75 | 0.198 | 15 | 0.242 | 1.222 |
| | | | 20 | 0.259 | 1.308 |
| | | | 25 | 0.246 | 1.242 |
| | | | 30 | 0.271 | 1.369 |
| | | | 35 | 0.231 | 1.167 |
| | | | 40 | 0.255 | 1.288 |
| | | | 45 | 0.270 | 1.364 |

For example, when the first irradiation angle was set to be any one of 50 to 65 degrees while varying the irradiation angle of the second irradiation beam (hereinafter, simply referred to as "second irradiation angle") from 15 to 20 degrees with respect to the wafer surface, the minimum of the ratio b1/a1 was found to be 1.367 (first irradiation angle: 65 degrees, second irradiation angle: 15 degrees) in case the defect on the wafer surface was a particle. On the other hand, in case the defect on the wafer surface was a pinhole, the maximum of the ratio b1/a1 was found to be 1.361 (first irradiation angle: 50 degrees, second irradiation angle: 20 degrees). Accordingly, this result indicates that it is possible to determine whether the defect on the wafer surface is a particle or a pinhole based on the value of the ratio b1/a1 by setting the threshold value of the ratio b1/a1 between 1.361 and 1.367.

Further, for instance, when the first irradiation angle was set to be any one of 60 to 70 degrees and the second irradiation angle was varied from 15 to 25 degrees with respect to the wafer surface, the minimum of the ratio b1/a1 was found to be 1.367 (first irradiation angle: 65 degrees, second irradiation angle: 15 degrees) in case the defect on the wafer surface was a particle. On the other hand, in case the defect on the wafer surface was a pinhole, the maximum of the ratio b1/a1 was found to be 1.337 (first irradiation angle: 65 degrees, second irradiation angle: 15 degrees). Accordingly, this result indicates that it is possible to determine whether the defect on the wafer surface is a particle or a pinhole based on the value of the ratio b1/a1 by setting the threshold value of the ratio b1/a1 between 1.337 and 1.367.

For another example, when the first irradiation angle was set to be any one of 65 to 75 degrees while varying the second irradiation angle from 15 to 20 degrees with respect to the wafer surface, the minimum of the ratio b1/a1 was found to be 1.222 (first irradiation angle: 75 degrees, second irradiation angle: 15 degrees) in case the defect on the wafer surface was a particle. On the other hand, in case the defect on the wafer surface was a pinhole, the maximum of the ratio b1/a1 was found to be 1.179 (first irradiation angle: 65 degrees, second irradiation angle: 20 degrees). This result indicates that it is possible to determine whether the defect on the wafer surface is a particle or a pinhole based on the value of the ratio b1/a1 by setting the threshold value of the ratio b1/a1 between 1.179 and 1.222.

With the above analysis results, it was found to be possible to determine whether a defect on a wafer surface is a particle or a pinhole based on a ratio of intensities of scattered lights by using the wafer surface inspection apparatus 10 by way of irradiating a laser beam Ls as a first irradiation beam at an irradiation angle $\alpha_1$ of 60 degrees or thereabout and further irradiating a laser beam Ls as a second irradiation beam by varying its irradiation angle $\alpha_1$ between, e.g., 15 to 45 degrees by using the laser beam illuminator 11, or alternately by way of installing another laser beam illuminator (not shown) such that it irradiates an s-polarized laser beam to an inspection site on a wafer surface at a fixed irradiation angle of 60 degrees or thereabout while concurrently fixing the laser beam illuminator 11 to irradiate a laser beam Ls at a small irradiation angle $\alpha_1$ ranging from, e.g., 15 to 45 degrees.

Based on the intensities of scattered lights obtained by varying an irradiation angle of the laser beam 44 from 5 to 90 degrees in the above analysis, a ratio of an intensity of the scattered light generated by an irradiation of an s-polarized laser beam to that by an irradiation of a p-polarized laser beam (scattered light's intensity at an irradiation of an s-polarization/scattered light's intensity at an irradiation of a p-polarization) (hereinafter, simply referred to as "intensity ratio of scattered lights") was observed for each of a particle and a pinhole, and the results were provided in a graph shown in FIG. 9.

Figure 9:
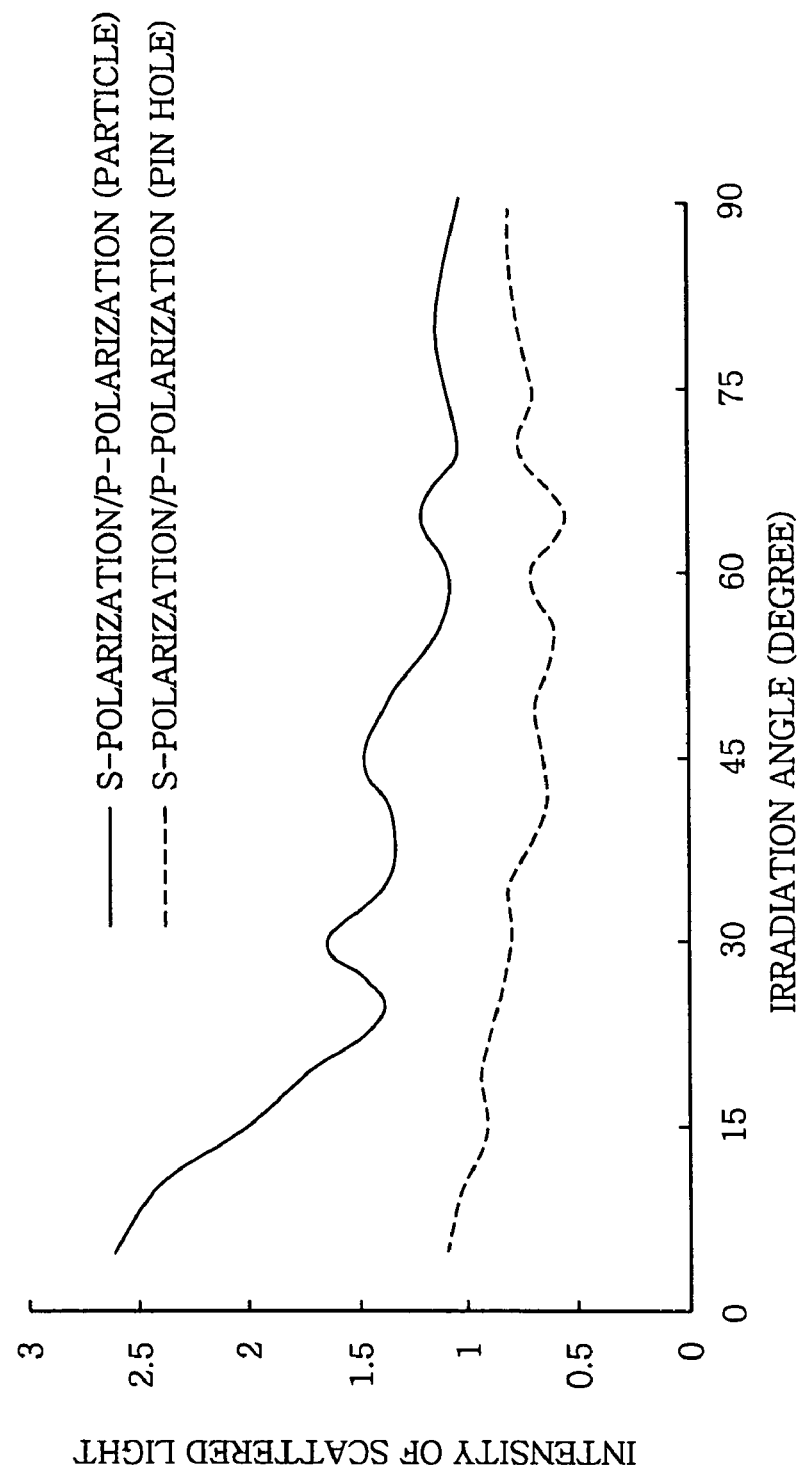
FIG. 9 shows a graph to describe variations in the ratio of the intensities of scattered lights generated by an irradiation of a p-polarized laser beam to the intensities of scattered lights generated by an irradiation of an s-polarized laser beam.

In FIG. 9, a solid line represents an intensity ratio of scattered lights from a particle while a dotted line refers to an intensity ratio of scattered lights from a pinhole.

From the graph shown in FIG. 9, it was found that the intensity ratio of scattered lights from a particle is greater than that from a pinhole at small irradiation angles. That is to say, it was found to be possible to determine a defect on a wafer surface based on the intensity ratio of scattered lights. Specifically, if the intensity ratio of scattered lights is great at small irradiation angles, the defect on the wafer surface would be determined as a particle; otherwise, it would be determined as a pinhole.

To be more specific, in case the irradiation angle of the laser beam 44 is varied between 15 and 45 degrees, the intensity ratio of scattered lights from a particle was greater than 1 while the intensity ratio of scattered lights from a pinhole was 1 or less. Thus, in case where the irradiation angle of the laser beam 44 is varied between 15 to 45 degrees, the defect on the wafer surface would be determined as a particle if the intensity ratio of scattered lights is greater than 1, whereas the defect would be determined as a pinhole if the intensity ratio of scattered lights is 1 or less. Thus, from the above analysis result, it was found to be possible to determine whether the defect F on the wafer surface is a particle or a pinhole by using the wafer surface inspection apparatus 10 by way of irradiating laser beams Ls and Lp from the laser beam illuminators 11 and 12 by varying their irradiation angles $\alpha_1$ and $\alpha_2$ within a small angular range of, e.g., 15 to 45 degrees or by fixing the laser beam illuminators 11 and 12 such that their irradiation angles $\alpha_1$ and $\alpha_2$ are between, e.g., 15 to 45 degrees, respectively.

Moreover, from the graph in FIG. 9, it was observed that, in case the irradiation angle of the laser beam 44 was varied from 5 to 25 degrees, the absolute value of a variation of the intensity ratio of scattered lights from a particle was greater than 1, whereas the absolute value of a variation of the intensity ratio of scattered lights from a pinhole was 1 or less. Thus, in case the irradiation angle of the laser beam 44 is varied between 5 to 25 degrees, a defect on a wafer surface would be determined as a particle if the absolute value of a variation of the intensity ratio of scattered lights is greater than 1, whereas the defect would be determined as a pinhole if the absolute value of a variation of the intensity ratio of scattered lights is 1 or less.

EXAMPLE 2

First, variations in the amplitude of scattered lights were analyzed by using electromagnetic wave analysis models for a pinhole and a particle shown in FIGS. 4A and 4B, respectively, while varying scattering angles (detection angles) of the scattered lights. At this time, the polarization component of a laser beam 44 was set to be a p-polarization or an s-polarization, and the irradiation angle of the laser beam 44 was set to be any one of 20 degrees or thereabout, 60 degrees or thereabout and 90 degrees or thereabout. Parameters used for this analysis were identical with those described above for the analysis of the intensity distribution of scattered lights. The analysis results were provided in graphs in FIGS. 10 to 12, wherein "amplitude of scattered light" in each drawing represents the ½ power of the amplitude of a scattered light that is incident on a certain area at each scattering angle. Further, in the drawings, a bold solid line represents the amplitudes of scattered lights from a particle when an s-polarized laser beam was irradiated; a solid line represents the amplitudes of scattered lights from a pinhole when an s-polarized laser beam was irradiated; a bold dotted line represents the amplitudes of scattered lights from a particle when a p-polarized laser beam was irradiated; and a dotted line represents the amplitudes of scattered lights from a pinhole when a p-polarized laser beam was irradiated.

Figure 10:
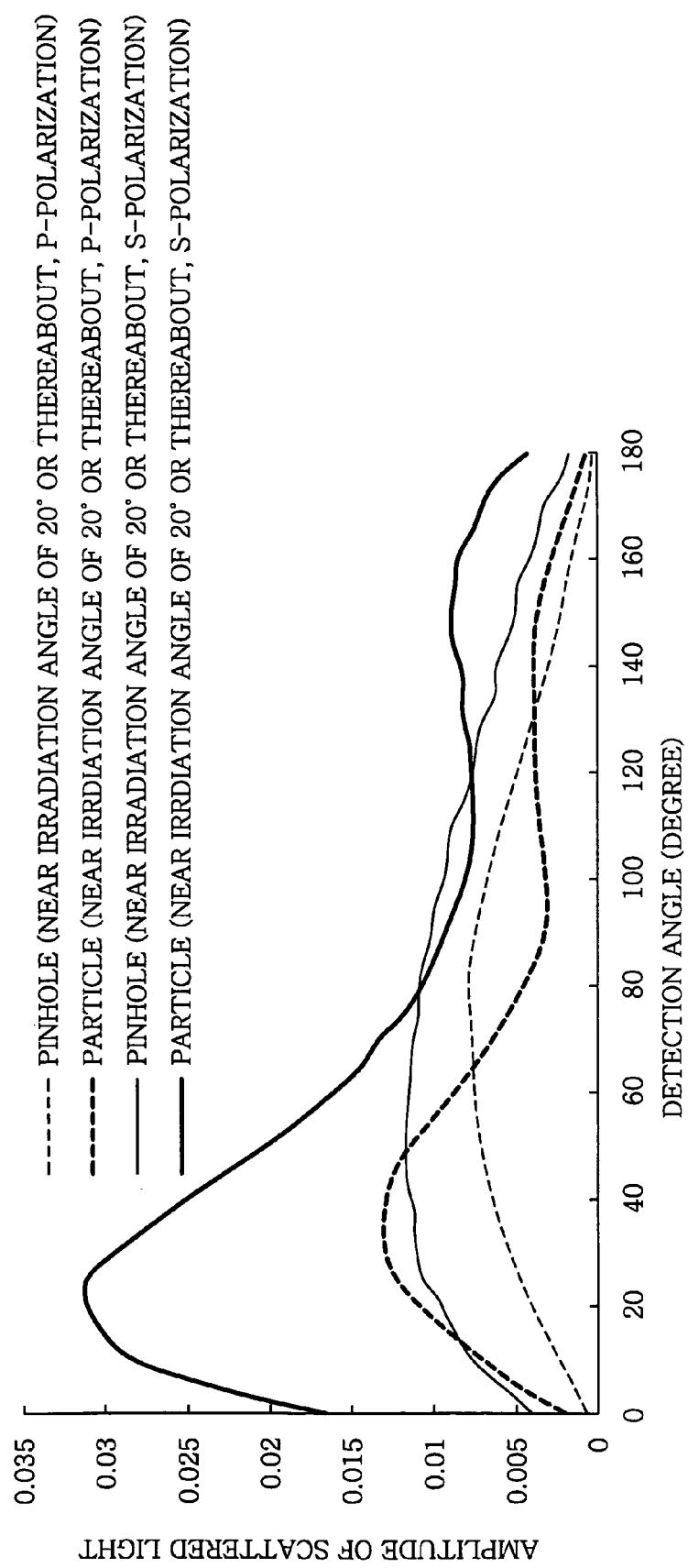
FIG. 10 sets forth a graph to describe variations in the amplitude of scattered lights detected by varying detection angles thereof when the irradiation angle of a laser beam is set to be 20 degrees or thereabout.

FIG. 10 presents a graph to describe variations in the amplitude of scattered lights when an irradiation angle of the laser beam 44 was set to be 20 degrees or thereabout.

As can be seen from the graph in FIG. 10, the amplitudes of the scattered lights from the particle were greater than the amplitudes of the scattered lights from the pinhole at small scattering angles when an s-polarized laser beam was applied. That is, the graph reveals that if the amplitudes of scattered lights generated by an s-polarized laser beam are great at a small scattering angle, a defect on a wafer surface can be determined as a particle; otherwise, it can be determined as a pinhole.

Specifically, when the scattering angle was 20 degrees or thereabout, the amplitudes of the scattered lights from the particle upon the irradiation of the s-polarized laser beam were found to have a peak value, whereas the amplitudes of the scattered lights from the pinhole upon the irradiation of the s-polarized laser beam were found to have no peak value. That is, if a peak value of the amplitude of the scattered lights due to the s-polarization is detected at the scattering angle of 20 degrees or thereabout, the defect on the wafer surface would be determined as a particle; otherwise, the defect would be determined as a pinhole.

To be more specific, after setting the irradiation angle of the laser beam 44 to be 20 degrees or thereabout, a first scattered light was detected at a detection angle ranging from 80 to 130 degrees with respect to the wafer surface and, at the same time, a second scattered light was detected at a detection angle ranging from 5 to 35 degrees with respect to the wafer surface. In this case, when the defect on the wafer surface was a particle, a ratio of the amplitude b2 of the second scattered light to the amplitude a2 of the first scattered light (b2/a2) was great; and when the defect was a pinhole, the ratio b2/a2 was small.

Variations of the ratio b2/a2 were provided in Tables 8 to 14. Here, Tables 8 to 14 show variations of the ratio b2/a2 in cases where the detection angle of the second scattered light (hereinafter, simply referred to as "second detection angle") was set to be 5, 10, 15, 20, 25, 30 and 35 degrees, respectively.

TABLE 8

| | First scattered light | | Second scattered light | | |
|---|---|---|---|---|---|
| | Detection Angle (Degree) | Amplitude: a2 | Detection Angle (Degree) | Amplitude: b2 | Ratio (b2/a2) |
| Pinhole (s-polarization) | 80 | 0.0107 | 5 | 0.0057 | 0.535 |
| | 85 | 0.0105 | | | 0.546 |
| | 90 | 0.0102 | | | 0.563 |
| | 95 | 0.0098 | | | 0.586 |
| | 100 | 0.0094 | | | 0.612 |
| | 105 | 0.0090 | | | 0.635 |
| | 110 | 0.0087 | | | 0.656 |
| | 115 | 0.0083 | | | 0.691 |
| | 120 | 0.0077 | | | 0.743 |
| | 125 | 0.0074 | | | 0.777 |
| | 130 | 0.0069 | | | 0.824 |
| Particle (s-polarization) | 80 | 0.0108 | 5 | 0.0278 | 2.563 |
| | 85 | 0.0100 | | | 2.773 |
| | 90 | 0.0093 | | | 2.993 |
| | 95 | 0.0087 | | | 3.197 |
| | 100 | 0.0082 | | | 3.410 |
| | 105 | 0.0078 | | | 3.564 |
| | 110 | 0.0077 | | | 3.629 |
| | 115 | 0.0077 | | | 3.633 |
| | 120 | 0.0076 | | | 3.658 |
| | 125 | 0.0076 | | | 3.647 |
| | 130 | 0.0080 | | | 3.485 |

TABLE 9

| | First scattered light | | Second scattered light | | |
|---|---|---|---|---|---|
| | Detection Angle (Degree) | Amplitude: a2 | Detection Angle (Degree) | Amplitude: b2 | Ratio (b2/a2) |
| Pinhole (s-polarization) | 80 | 0.0107 | 10 | 0.0076 | 0.706 |
| | 85 | 0.0105 | | | 0.720 |
| | 90 | 0.0102 | | | 0.743 |
| | 95 | 0.0098 | | | 0.773 |
| | 100 | 0.0094 | | | 0.807 |
| | 105 | 0.0090 | | | 0.838 |
| | 110 | 0.0087 | | | 0.865 |
| | 115 | 0.0083 | | | 0.911 |
| | 120 | 0.0077 | | | 0.980 |
| | 125 | 0.0074 | | | 1.025 |
| | 130 | 0.0069 | | | 1.088 |
| Particle (s-polarization) | 80 | 0.0108 | 10 | 0.0278 | 2.563 |
| | 85 | 0.0100 | | | 2.773 |
| | 90 | 0.0093 | | | 2.993 |
| | 95 | 0.0087 | | | 3.197 |
| | 100 | 0.0082 | | | 3.410 |
| | 105 | 0.0078 | | | 3.564 |
| | 110 | 0.0077 | | | 3.629 |
| | 115 | 0.0077 | | | 3.633 |
| | 120 | 0.0076 | | | 3.658 |
| | 125 | 0.0076 | | | 3.647 |
| | 130 | 0.0080 | | | 3.485 |

TABLE 10

| | First scattered light | | Second scattered light | | |
|---|---|---|---|---|---|
| | Detection Angle (Degree) | Amplitude: a2 | Detection Angle (Degree) | Amplitude: b2 | Ratio (b2/a2) |
| Pinhole (s-polarization) | 80 | 0.0107 | 15 | 0.0067 | 0.813 |
| | 85 | 0.0105 | | | 0.830 |
| | 90 | 0.0102 | | | 0.855 |
| | 95 | 0.0098 | | | 0.890 |
| | 100 | 0.0094 | | | 0.929 |
| | 105 | 0.0090 | | | 0.965 |
| | 110 | 0.0087 | | | 0.996 |
| | 115 | 0.0083 | | | 1.049 |
| | 120 | 0.0077 | | | 1.128 |
| | 125 | 0.0074 | | | 1.180 |
| | 130 | 0.0069 | | | 1.252 |
| Particle (s-polarization) | 80 | 0.0108 | 15 | 0.0301 | 2.777 |
| | 85 | 0.0100 | | | 3.004 |
| | 90 | 0.0093 | | | 3.244 |
| | 95 | 0.0087 | | | 3.464 |
| | 100 | 0.0082 | | | 3.695 |
| | 105 | 0.0078 | | | 3.862 |
| | 110 | 0.0077 | | | 3.933 |
| | 115 | 0.0077 | | | 3.936 |
| | 120 | 0.0076 | | | 3.964 |
| | 125 | 0.0076 | | | 3.951 |
| | 130 | 0.0080 | | | 3.776 |

TABLE 11

| | First scattered light | | Second scattered light | | |
|---|---|---|---|---|---|
| | Detection Angle (Degree) | Amplitude: a2 | Detection Angle (Degree) | Amplitude: b2 | Ratio (b2/a2) |
| Pinhole (s-polarization) | 80 | 0.0107 | 20 | 0.0095 | 0.886 |
| | 85 | 0.0105 | | | 0.904 |
| | 90 | 0.0102 | | | 0.931 |
| | 95 | 0.0098 | | | 0.970 |
| | 100 | 0.0094 | | | 1.012 |
| | 105 | 0.0090 | | | 1.051 |
| | 110 | 0.0087 | | | 1.085 |
| | 115 | 0.0083 | | | 1.143 |
| | 120 | 0.0077 | | | 1.229 |
| | 125 | 0.0074 | | | 1.286 |
| | 130 | 0.0069 | | | 1.364 |
| Particle (s-polarization) | 80 | 0.0108 | 20 | 0.0312 | 2.876 |
| | 85 | 0.0100 | | | 3.111 |
| | 90 | 0.0093 | | | 3.359 |
| | 95 | 0.0087 | | | 3.587 |
| | 100 | 0.0082 | | | 3.826 |
| | 105 | 0.0078 | | | 3.999 |
| | 110 | 0.0077 | | | 4.072 |
| | 115 | 0.0077 | | | 4.076 |
| | 120 | 0.0076 | | | 4.105 |
| | 125 | 0.0076 | | | 4.091 |
| | 130 | 0.0080 | | | 3.910 |

TABLE 12

| | First scattered light | | Second scattered light | | |
|---|---|---|---|---|---|
| | Detection Angle (Degree) | Amplitude: a2 | Detection Angle (Degree) | Amplitude: b2 | Ratio (b2/a2) |
| Pinhole (s-polarization) | 80 | 0.0107 | 25 | 0.0104 | 0.976 |
| | 85 | 0.0105 | | | 0.996 |
| | 90 | 0.0102 | | | 1.027 |
| | 95 | 0.0098 | | | 1.069 |
| | 100 | 0.0094 | | | 1.116 |
| | 105 | 0.0090 | | | 1.158 |
| | 110 | 0.0087 | | | 1.196 |
| | 115 | 0.0083 | | | 1.260 |
| | 120 | 0.0077 | | | 1.354 |
| | 125 | 0.0074 | | | 1.417 |
| | 130 | 0.0069 | | | 1.503 |
| Particle (s-polarization) | 80 | 0.0108 | 25 | 0.0312 | 2.873 |
| | 85 | 0.0100 | | | 3.107 |
| | 90 | 0.0093 | | | 3.355 |
| | 95 | 0.0087 | | | 3.583 |
| | 100 | 0.0082 | | | 3.822 |
| | 105 | 0.0078 | | | 3.995 |
| | 110 | 0.0077 | | | 4.068 |
| | 115 | 0.0077 | | | 4.072 |
| | 120 | 0.0076 | | | 4.100 |
| | 125 | 0.0076 | | | 4.087 |
| | 130 | 0.0080 | | | 3.906 |

TABLE 13

| | First scattered light | | Second scattered light | | |
|---|---|---|---|---|---|
| | Detection Angle (Degree) | Amplitude: a2 | Detection Angle (Degree) | Amplitude: b2 | Ratio (b2/a2) |
| Pinhole (s-polarization) | 80 | 0.0107 | 30 | 0.0109 | 1.023 |
| | 85 | 0.0105 | | | 1.044 |
| | 90 | 0.0102 | | | 1.076 |
| | 95 | 0.0098 | | | 1.120 |
| | 100 | 0.0094 | | | 1.169 |
| | 105 | 0.0090 | | | 1.214 |
| | 110 | 0.0087 | | | 1.253 |
| | 115 | 0.0083 | | | 1.320 |
| | 120 | 0.0077 | | | 1.419 |
| | 125 | 0.0074 | | | 1.485 |
| | 130 | 0.0069 | | | 1.575 |
| Particle (s-polarization) | 80 | 0.0108 | 30 | 0.0296 | 2.727 |
| | 85 | 0.0100 | | | 2.950 |
| | 90 | 0.0093 | | | 3.185 |
| | 95 | 0.0087 | | | 3.402 |
| | 100 | 0.0082 | | | 3.628 |
| | 105 | 0.0078 | | | 3.792 |
| | 110 | 0.0077 | | | 3.862 |
| | 115 | 0.0077 | | | 3.865 |
| | 120 | 0.0076 | | | 3.893 |
| | 125 | 0.0076 | | | 3.880 |
| | 130 | 0.0080 | | | 3.708 |

TABLE 14

| | First scattered light | | Second scattered light | | |
|---|---|---|---|---|---|
| | Detection Angle (Degree) | Amplitude: a2 | Detection Angle (Degree) | Amplitude: b2 | Ratio (b2/a2) |
| Pinhole (s-polarization) | 80 | 0.0107 | 35 | 0.0110 | 1.033 |
| | 85 | 0.0105 | | | 1.054 |
| | 90 | 0.0102 | | | 1.086 |
| | 95 | 0.0098 | | | 1.131 |
| | 100 | 0.0094 | | | 1.181 |
| | 105 | 0.0090 | | | 1.225 |

TABLE 14-continued

| | First scattered light | | Second scattered light | | |
|---|---|---|---|---|---|
| | Detection Angle (Degree) | Amplitude: a2 | Detection Angle (Degree) | Amplitude: b2 | Ratio (b2/a2) |
| | 110 | 0.0087 | | | 1.265 |
| | 115 | 0.0083 | | | 1.333 |
| | 120 | 0.0077 | | | 1.433 |
| | 125 | 0.0074 | | | 1.499 |
| | 130 | 0.0069 | | | 1.591 |
| Particle (s-polarization) | 80 | 0.0108 | 35 | 0.0253 | 2.334 |
| | 85 | 0.0100 | | | 2.524 |
| | 90 | 0.0093 | | | 2.725 |
| | 95 | 0.0087 | | | 2.911 |
| | 100 | 0.0082 | | | 3.105 |
| | 105 | 0.0078 | | | 3.245 |
| | 110 | 0.0077 | | | 3.304 |
| | 115 | 0.0077 | | | 3.308 |
| | 120 | 0.0076 | | | 3.331 |
| | 125 | 0.0076 | | | 3.320 |
| | 130 | 0.0080 | | | 3.173 |

At this time, in case the defect on the wafer surface is a particle, the minimum of the ratio b2/a2 was found to be 2.333 (detection angle of the first scattered light (hereinafter, simply referred to as "first detection angle"): 80 degrees, second detection angle: 35 degrees). On the other hand, in case the defect on the wafer surface is a pinhole, the maximum of the ratio b2/a2 was found to be 1.591 (first detection angle: 130 degrees, second detection angle: 35 degrees). Thus, this result indicates that it is possible to determine whether the defect on the wafer surface is a particle or a pinhole based on the value of the ratio b2/a2 by setting the threshold value of the ratio b2/a2 between 1.591 and 2.334.

With the above analysis result, it was found to be possible to determine whether a defect on a wafer surface is a particle or a pinhole based on a ratio of the amplitudes of scattered lights by using the wafer surface inspection apparatus 70 by way of irradiating a laser beam Ls from the laser beam illuminator 11 at an irradiation angle $\alpha_1$ of 20 degrees or thereabout; detecting a first scattered light Ss by means of the scattered light detector 71 at a detection angle $\beta_1$ ranging from 80 to 130 degrees; and also detecting a second scattered light Ss at a small detection angle $\beta_1$ of, e.g., 20 degrees or thereabout, or alternatively by way of installing another scattered light detector (not shown) such that it detects a scattered light Ss generated by a laser beam Ls at a detection angle ranging from 80 to 130 degrees and, at the same time, fixing the scattered light detector 71 such that it detects a scattered light Ss at a small detection angle $\beta_1$ of, e.g., 20 degrees or thereabout.

Figure 11:
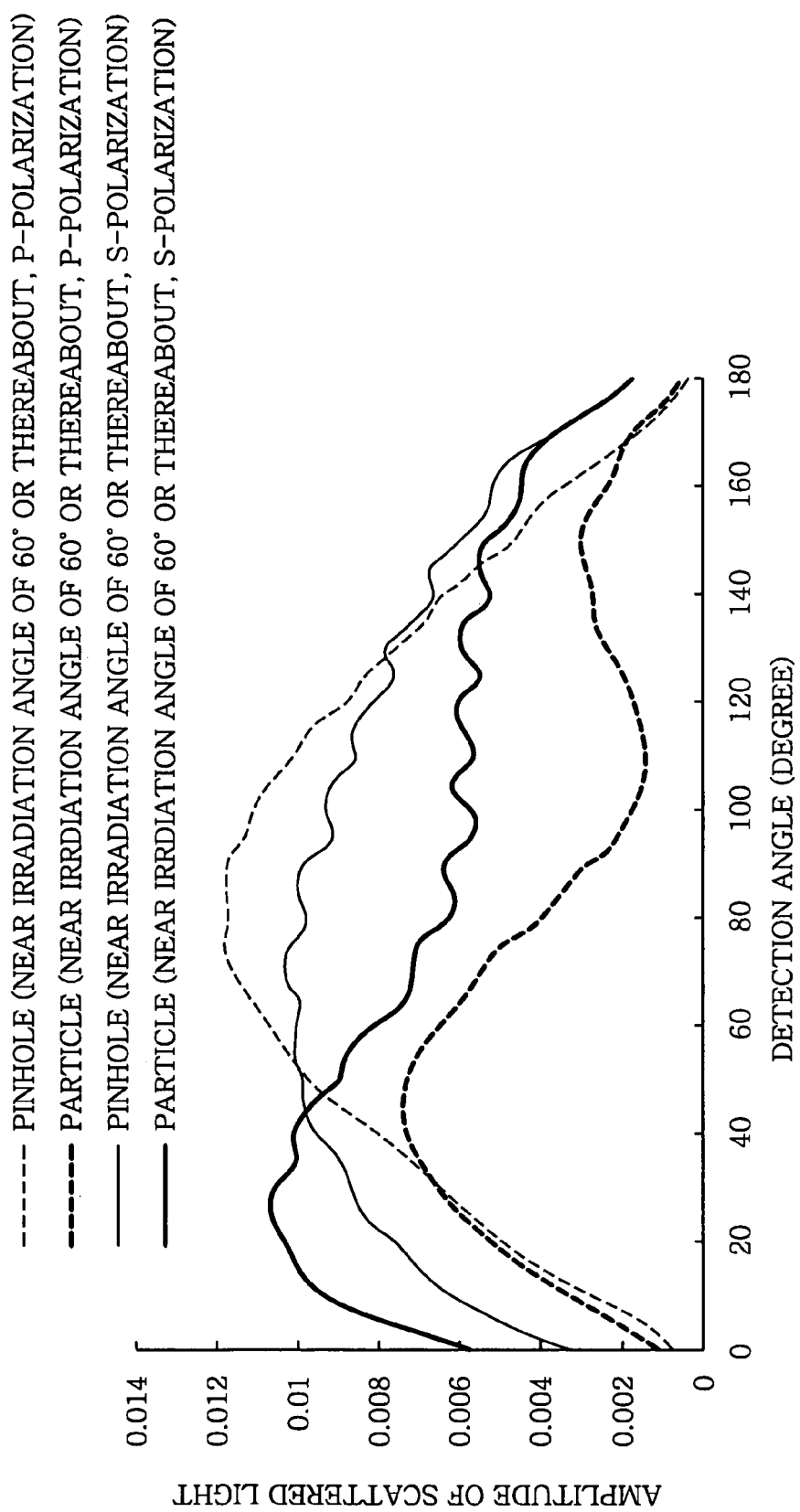
FIG. 11 illustrate a graph to describe variations in the amplitude of scattered lights detected by varying detection angles thereof when the irradiation angle of a laser beam is set to be 60 degrees or thereabout.

FIG. 11 sets forth a graph to describe variations of the amplitudes of scattered lights when the laser beam 44 was irradiated at an irradiation angle of 60 degrees or thereabout.

From the graph in FIG. 11, it was found that the amplitudes of the scattered lights generated from the pinhole were greater than those of the scattered lights from the particle at large scattering angles when a p-polarized laser beam was irradiated. That is, if the amplitude of a scattered light generated by the p-polarized laser beam is great at a large scattering angle, a defect on a wafer surface would be determined as a particle; otherwise, the defect would be determined as a particle.

Figure 12:
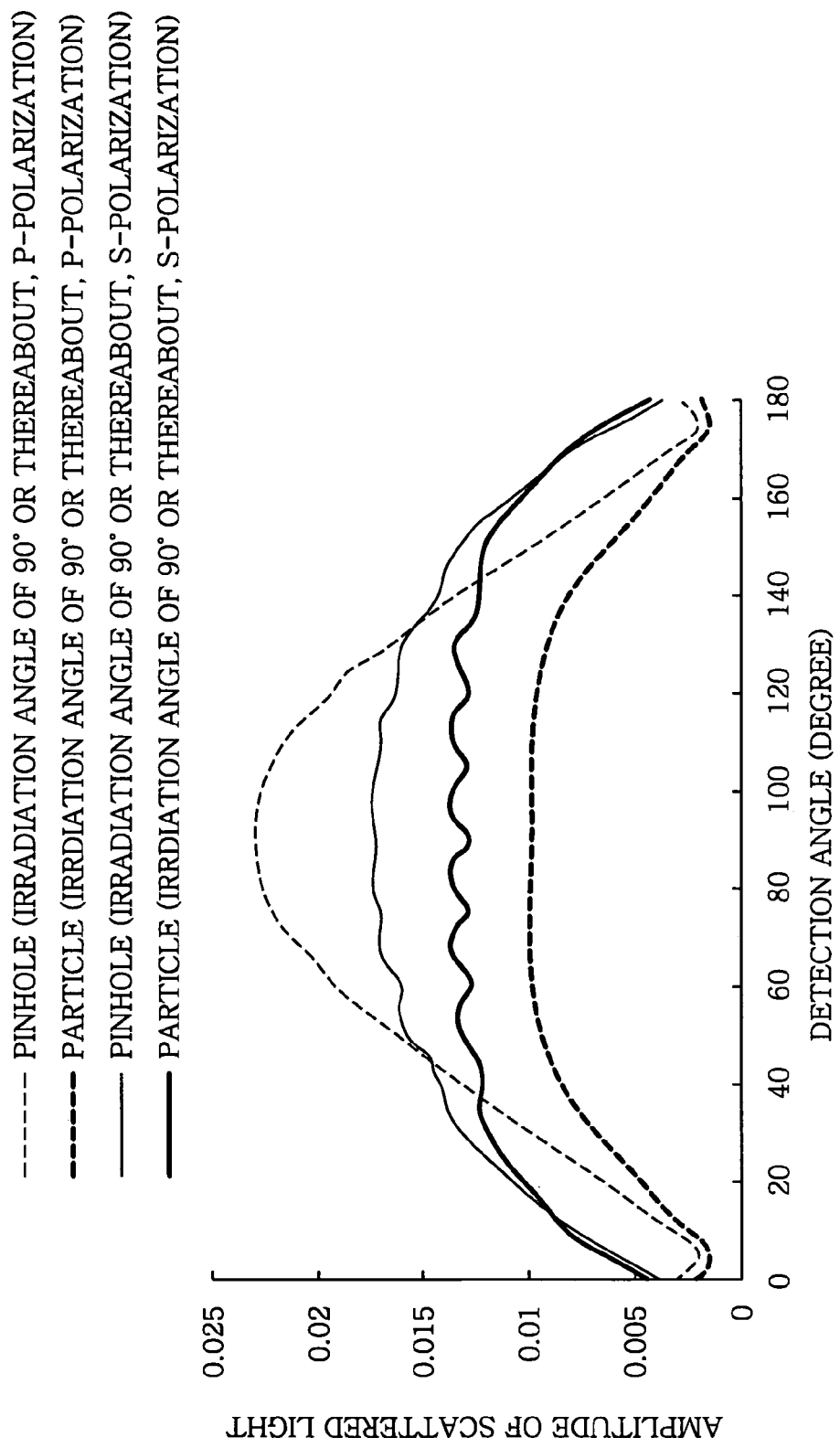
FIG. 12 presents a graph to describe variations in the amplitude of scattered lights detected by varying detection angles thereof when the irradiation angle of a laser beam is set to be 90 degrees or thereabout.

FIG. 12 shows a graph to describe variations of the amplitudes of scattered lights when the laser beam 44 was irradiated at an irradiation angle of 90 degrees or thereabout.

From the graph in FIG. 12, it was observed that the amplitudes of the scattered lights from the pinhole were greater than those of the scattered lights from the particle at large scattering angles when a p-polarized laser beam was irradiated. That is, if the amplitude of a scattered light generated by the p-polarized laser beam is great at a large scattering angle, a defect on a wafer surface would be determined as a pinhole; otherwise, the defect would be determined as a particle.

Specifically, at a scattering angle of 90 degrees or thereabout, when a p-polarized laser beam was irradiated, the amplitudes of the scattered lights from the pinhole were found to have a peak value, whereas the amplitudes of the scattered lights from the particle were found to have no peak value. That is, if a peak value of the amplitudes of the scattered lights due to the p-polarization is detected at a scattering angle of 90 degrees or thereabout, a defect on a wafer surface would be determined as a pinhole; otherwise, the defect would be determined as a particle.

To be more specific, after setting the irradiation angle of the laser beam 44 to be 90 degrees or thereabout, a first scattered light was detected at a detection angle ranging from 40 to 60 degrees with respect to the wafer surface and, at the same time, a second scattered light was detected at a detection angle ranging from 75 to 105 degrees with respect to the wafer surface. In this case, when the defect on the wafer surface was a pinhole, a ratio of the amplitude b3 of the second scattered light to the amplitude a3 of the first scattered light (b3/a3) was great; and when the defect was a particle, the ratio b3/a3 was small.

Variations of the ratio b3/a3 were provided in Tables 15 to 21. Here, Tables 15 to 21 show variations of the ratio b3/a3 in cases where the second detection angle was set to be 75, 80, 85, 90, 95, 100 and 105 degrees, respectively.

TABLE 15

| | First scattered light | | Second scattered light | | |
|---|---|---|---|---|---|
| | Detection Angle (Degree) | Amplitude: a3 | Detection Angle (Degree) | Amplitude: b3 | Ratio (b3/a3) |
| Pinhole (p-polarization) | 40 | 0.0131 | 75 | 0.0220 | 1.685 |
| | 45 | 0.0146 | | | 1.506 |
| | 50 | 0.0162 | | | 1.360 |
| | 55 | 0.0178 | | | 1.234 |
| | 60 | 0.0190 | | | 1.155 |
| Particle (p-polarization) | 40 | 0.0082 | 75 | 0.0098 | 1.203 |
| | 45 | 0.0087 | | | 1.129 |
| | 50 | 0.0091 | | | 1.076 |
| | 55 | 0.0095 | | | 1.032 |
| | 60 | 0.0097 | | | 1.019 |

TABLE 16

| | First scattered light | | Second scattered light | | |
|---|---|---|---|---|---|
| | Detection Angle (Degree) | Amplitude: a3 | Detection Angle (Degree) | Amplitude: b3 | Ratio (b3/a3) |
| Pinhole (p-polarization) | 40 | 0.0131 | 80 | 0.0226 | 1.728 |
| | 45 | 0.0146 | | | 1.544 |
| | 50 | 0.0162 | | | 1.395 |

TABLE 16-continued

| | First scattered light | | Second scattered light | | |
|---|---|---|---|---|---|
| | Detection Angle (Degree) | Amplitude: a3 | Detection Angle (Degree) | Amplitude: b3 | Ratio (b3/a3) |
| | 55 | 0.0178 | | | 1.266 |
| | 60 | 0.0190 | | | 1.184 |
| Particle (p-polarization) | 40 | 0.0082 | 80 | 0.0098 | 1.204 |
| | 45 | 0.0087 | | | 1.130 |
| | 50 | 0.0091 | | | 1.076 |
| | 55 | 0.0095 | | | 1.033 |
| | 60 | 0.0097 | | | 1.020 |

TABLE 17

| | First scattered light | | Second scattered light | | |
|---|---|---|---|---|---|
| | Detection Angle (Degree) | Amplitude: a3 | Detection Angle (Degree) | Amplitude: b3 | Ratio (b3/a3) |
| Pinhole (p-polarization) | 40 | 0.0131 | 85 | 0.0228 | 1.750 |
| | 45 | 0.0146 | | | 1.564 |
| | 50 | 0.0162 | | | 1.413 |
| | 55 | 0.0178 | | | 1.282 |
| | 60 | 0.0190 | | | 1.200 |
| Particle (p-polarization) | 40 | 0.0082 | 85 | 0.0098 | 1.201 |
| | 45 | 0.0087 | | | 1.127 |
| | 50 | 0.0091 | | | 1.074 |
| | 55 | 0.0095 | | | 1.030 |
| | 60 | 0.0097 | | | 1.017 |

TABLE 18

| | First scattered light | | Second scattered light | | |
|---|---|---|---|---|---|
| | Detection Angle (Degree) | Amplitude: a3 | Detection Angle (Degree) | Amplitude: b3 | Ratio (b3/a3) |
| Pinhole (p-polarization) | 40 | 0.0131 | 90 | 0.0230 | 1.761 |
| | 45 | 0.0146 | | | 1.574 |
| | 50 | 0.0162 | | | 1.421 |
| | 55 | 0.0178 | | | 1.290 |
| | 60 | 0.0190 | | | 1.207 |
| Particle (p-polarization) | 40 | 0.0082 | 90 | 0.0097 | 1.192 |
| | 45 | 0.0087 | | | 1.119 |
| | 50 | 0.0091 | | | 1.066 |
| | 55 | 0.0095 | | | 1.023 |
| | 60 | 0.0097 | | | 1.010 |

TABLE 19

| | First scattered light | | Second scattered light | | |
|---|---|---|---|---|---|
| | Detection Angle (Degree) | Amplitude: a3 | Detection Angle (Degree) | Amplitude: b3 | Ratio (b3/a3) |
| Pinhole (p-polarization) | 40 | 0.0131 | 95 | 0.0229 | 1.758 |
| | 45 | 0.0146 | | | 1.571 |
| | 50 | 0.0162 | | | 1.419 |
| | 55 | 0.0178 | | | 1.288 |
| | 60 | 0.0190 | | | 1.205 |
| Particle (p-polarization) | 40 | 0.0082 | 95 | 0.0098 | 1.197 |
| | 45 | 0.0087 | | | 1.123 |
| | 50 | 0.0091 | | | 1.070 |

TABLE 19-continued

| | First scattered light | | Second scattered light | | |
|---|---|---|---|---|---|
| | Detection Angle (Degree) | Amplitude: a3 | Detection Angle (Degree) | Amplitude: b3 | Ratio (b3/a3) |
| | 55 | 0.0095 | | | 1.027 |
| | 60 | 0.0097 | | | 1.014 |

TABLE 20

| | First scattered light | | Second scattered light | | |
|---|---|---|---|---|---|
| | Detection Angle (Degree) | Amplitude: a3 | Detection Angle (Degree) | Amplitude: b3 | Ratio (b3/a3) |
| Pinhole (p-polarization) | 40 | 0.0131 | 100 | 0.0228 | 1.745 |
| | 45 | 0.0146 | | | 1.599 |
| | 50 | 0.0162 | | | 1.408 |
| | 55 | 0.0178 | | | 1.278 |
| | 60 | 0.0190 | | | 1.196 |
| Particle (p-polarization) | 40 | 0.0082 | 100 | 0.0098 | 1.200 |
| | 45 | 0.0087 | | | 1.126 |
| | 50 | 0.0091 | | | 1.073 |
| | 55 | 0.0095 | | | 1.030 |
| | 60 | 0.0097 | | | 1.017 |

TABLE 21

| | First scattered light | | First scattered light | | |
|---|---|---|---|---|---|
| | Detection Angle (Degree) | Amplitude: a3 | Detection Angle (Degree) | Amplitude: b3 | Ratio (b3/a3) |
| Pinhole (p-polarization) | 40 | 0.0131 | 105 | 0.0223 | 1.707 |
| | 45 | 0.0146 | | | 1.526 |
| | 50 | 0.0162 | | | 1.378 |
| | 55 | 0.0178 | | | 1.250 |
| | 60 | 0.0190 | | | 1.170 |
| Particle (p-polarization) | 40 | 0.0082 | 105 | 0.0098 | 1.194 |
| | 45 | 0.0087 | | | 1.121 |
| | 50 | 0.0091 | | | 1.068 |
| | 55 | 0.0095 | | | 1.024 |
| | 60 | 0.0097 | | | 1.011 |

For example, in case the defect on the wafer surface is a pinhole, by setting the first detection angle as any one of 40 to 55 degrees while varying the second angle between 75 to 105 degrees with respect to the wafer surface, the minimum of the ratio b3/a3 was found to be 1.234 (first detection angle: 55 degrees, second detection angle: 75 degrees). On the other hand, in case the defect on the wafer surface is a particle, the maximum of the ratio b3/a3 was found to be 1.204 (first detection angle: 40 degrees, second detection angle: 75 degrees). Thus, this result indicates that it is possible to determine whether the defect on the wafer surface is a particle or a pinhole based on the value of the ratio b3/a3 by setting the threshold value of the ratio b3/a3 between 1.204 and 1.234.

With the above analysis result, it was found to be possible to determine whether a defect on a wafer surface is a particle or a pinhole based on a ratio of the amplitudes of scattered lights by using the wafer surface inspection apparatus 70 by way of irradiating a laser beam Lp from the laser beam illuminator 12 at an irradiation angle of 90 degrees or thereabout; detecting a first scattered light Sp by means of the scattered light detector 71 at a detection angle $\beta_2$ ranging from 40 to 60 degrees; and also detecting a second scattered light Sp at a large detection angle $\beta_2$ of, e.g., 90 degrees or thereabout, or alternatively by way of installing another scattered light detector (not shown) such that it detects a scattered light Sp generated by a laser beam Lp at a detection angle ranging from 40 to 60 degrees and, at the same time, fixing the scattered light detector 72 such that it detects a scattered light Sp at a large detection angle $\beta_2$ of, e.g., 90 degrees or thereabout.

Further, as can be seen from the graphs in FIGS. 10 to 12, the amplitudes of scattered lights from the particle were great at small scattering angles when the s-polarized laser beam was irradiated at a small irradiation angle, whereas the amplitudes of scattered lights from the pinhole were great at large scattering angles when the p-polarized laser beam was irradiated at a large irradiation angle. That is, if the amplitude of a scattered light generated by an irradiation of an s-polarized laser beam at a small irradiation angle is great at a small scattering angle, a defect on a wafer surface would be determined as a particle; and if the amplitude of a scattered light generated by an irradiation of a p-polarized laser beam at a large irradiation angle is great at a large scattering angle, the defect on the wafer surface would be determined as a pinhole.

Specifically, the amplitudes of the scattered lights generated from the particle by the irradiation of the s-polarized laser beam at the irradiation angle of 20 degrees or thereabout were found to have a peak value at a scattering angle of 20 degrees or thereabout, and the amplitudes of the scattered lights generated from the pinhole by the irradiation of the p-polarized laser beam at the irradiation angle of 90 degrees or thereabout were found to have a peak value at a scattering angle of 90 degrees or thereabout. That is, if a peak value of the amplitudes of the scattered lights generated by the irradiation of an s-polarization beam at an irradiation angle of 20 degrees or thereabout is detected at a scattering angles of 20 degrees or thereabout, a defect on a wafer surface would be determined as a particle; and if a peak value of the amplitudes of the scattered lights generated by the irradiation of a p-polarization beam at an irradiation angle of 90 degrees or thereabout is detected at a scattering angle of 90 degrees or thereabout, the defect would be determined as a pinhole.

Based on the above analysis result, it was found to be possible to determine whether a defect on a wafer surface is a particle or a pinhole based on a peak value of the amplitudes of scattered lights by using the wafer surface inspection apparatus 70 by way of irradiating a laser beam Ls from the laser beam illuminator 11 at an irradiation angle of 20 degrees or thereabout; irradiating a laser beam Lp from the laser beam illuminator 12 at an irradiation angle of 90 degrees or thereabout; detecting scattered lights Ss by using the scattered light detector 71 at a small detection angle $\beta_1$ which is varied at, e.g., 20 degrees or thereabout; and also detecting scattered lights Sp by using the scattered light detector 72 at a large detection angle $\beta_2$ which is varied at, e.g., 90 degrees or thereabout.

EXAMPLE 3

Next, variations in the difference between the amplitudes of scattered lights from a particle and the amplitudes of scattered lights from a pinhole (amplitudes of scattered lights from the particle—amplitudes of scattered lights from the pinhole) (hereinafter, simply referred to as "amplitude difference of scattered lights") were analyzed by using electromagnetic wave analysis models for a pinhole and a particle shown in FIGS. 4A and 4B, respectively, while varying scattering angles (detection angles) of the scattered lights.

At this time, the polarization component of a laser beam 44 was set to be a p-polarization or an s-polarization, and the irradiation angle of the laser beam 44 was set to be any one of 15 degrees or thereabout, 20 degrees or thereabout, 45 degrees or thereabout, 60 degrees or thereabout and 90 degrees or thereabout. Parameters used for this analysis were identical with those described before for the analysis of the intensity distribution of scattered lights. The analysis results were provided in graphs in FIGS. 13 and 14, wherein a bold solid line, a bold dotted line, a solid line, a dotted line and a dashed dotted line represent amplitude differences of scattered lights in cases where the irradiation angle of the laser beam was set to be 15 degrees or thereabout, 20 degrees or thereabout, 45 degrees or thereabout, 60 degrees or thereabout and 90 degrees or thereabout, respectively.

Figure 13:
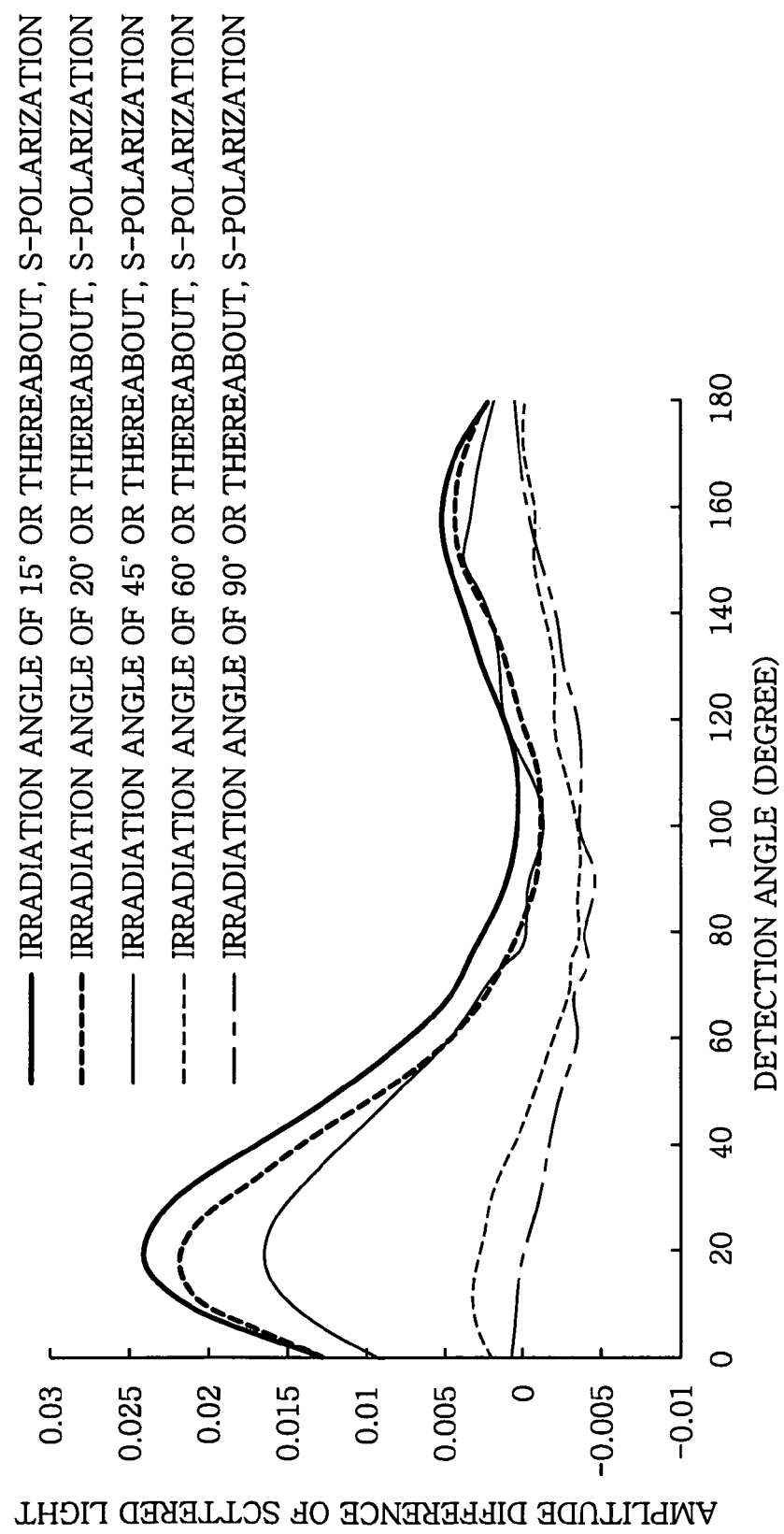
FIG. 13 depicts a graph to describe variations in the difference between the intensities of scattered lights from a particle and the intensities of scattered lights from a pinhole (intensities of scattered lights from a particle—intensities of scattered lights from a pinhole) when the polarization component of the laser beam 44 was set to be an s-polarization.

FIG. 13 presents a graph to describe variations in the amplitude difference of scattered lights when the polarization component of the laser beam 44 was set to be an s-polarization.

From the graph in FIG. 13, it was observed that, in case of small scattering angles, the amplitude differences of scattered lights were much greater in the case where the irradiation angle of the s-polarized laser beam was small than in the case where the irradiation angle of the s-polarized laser beam was large. That is, in case of irradiating an s-polarized laser beam, it was found to be possible to determine whether a defect on a wafer surface is a particle or a pinhole by setting the irradiation angle of the laser beam to be small and detecting a scattered light generated by the irradiated laser beam at a small scattering angle.

Figure 14:
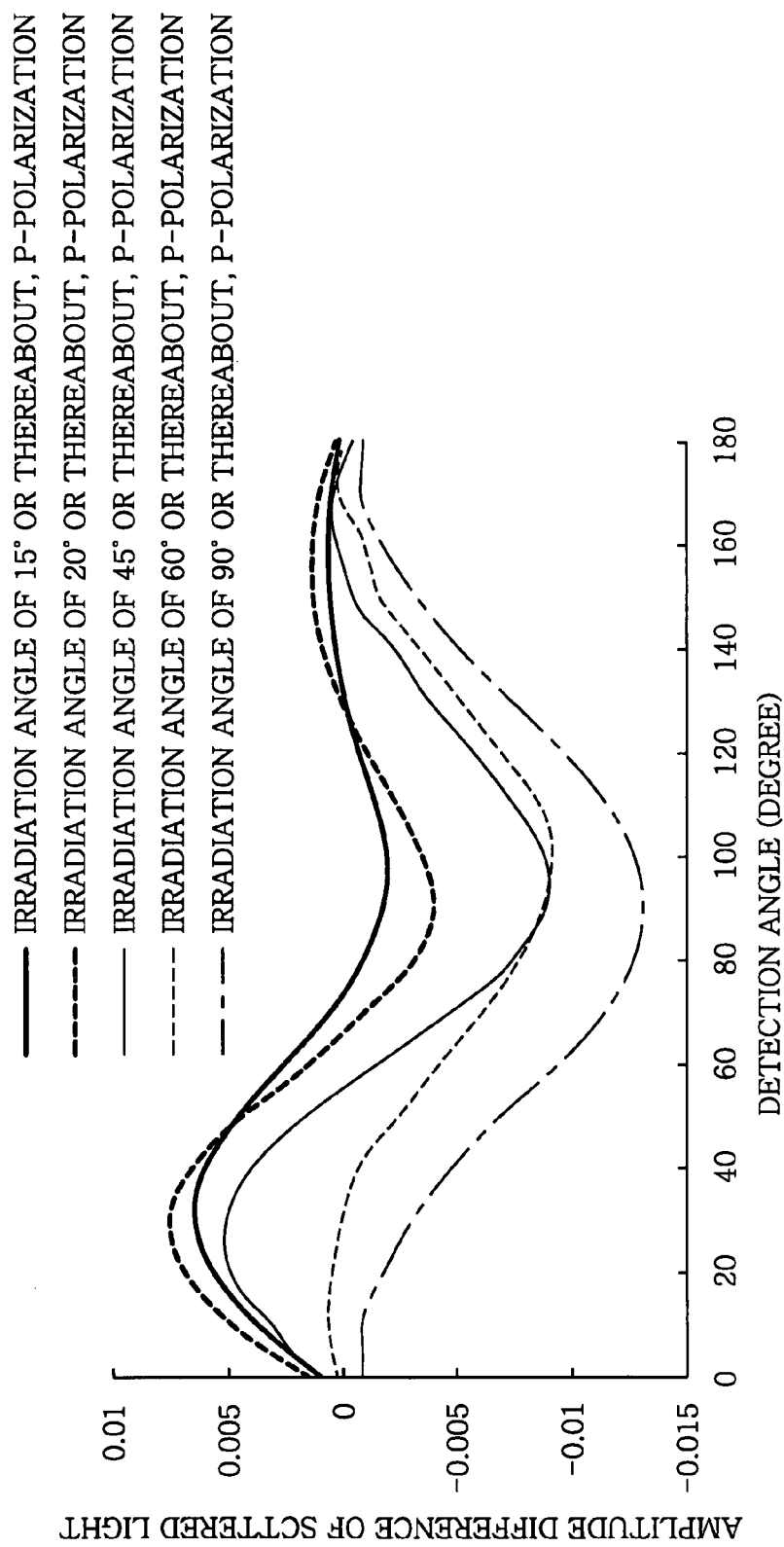
FIG. 14 shows a graph to describe variations in the difference between the intensities of scattered lights from a particle and the intensities of scattered lights from a pinhole (intensities of scattered lights from a particle—intensities of scattered lights from a pinhole) when the polarization component of the laser beam 44 was set to be a p-polarization.
Figure 15:
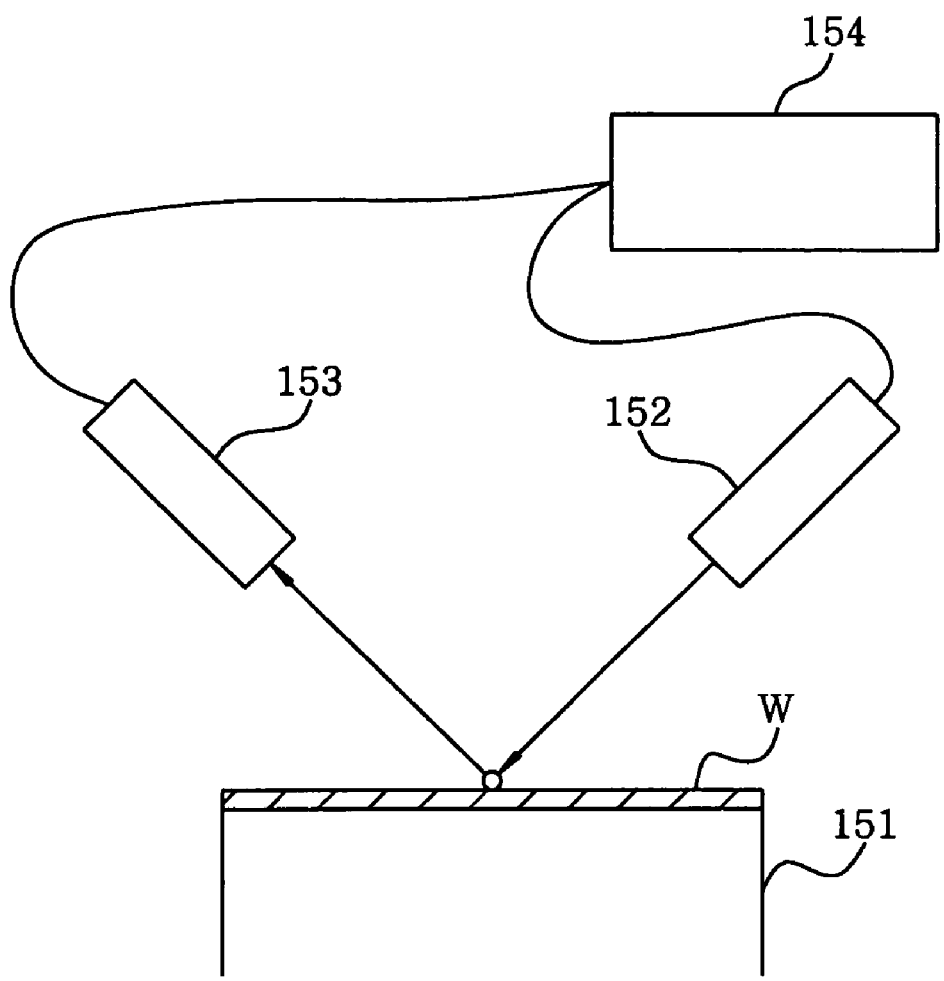
FIG. 15 provides a schematic configuration view of a conventional object surface inspection apparatus.

FIG. 14 sets forth a graph to describe variations in the amplitude difference of scattered lights when the polarization component of the laser beam 44 was set to be a p-polarization.

From the graph in FIG. 14, it was observed that, in case of large scattering angles, the amplitude differences of scattered lights were much smaller in the case where the irradiation angle of the p-polarized laser beam was large than in the case where the irradiation angle of the p-polarized laser beam was small. That is, in case of irradiating a p-polarized laser beam, it was found to be possible to determine whether a defect on a wafer surface is a particle or a pinhole by setting the irradiation angle of the laser beam to be large and detecting a scattered light generated by the irradiated laser beam at a large scattering angle.

While the invention has been shown and described with respect to the preferred embodiments, it will be understood by those skilled in the art that various changes and modifications may be made without departing from the spirit and scope of the invention as defined in the following claims.

What is claimed is:

1. An apparatus for inspecting a surface of an object to be processed, comprising:

at least one irradiation unit for irradiating a light on the surface of the object;

at least one detection unit for detecting a light scattered from the surface of the object in response to the irradiated light; and a determination unit for determining a cause of the scattered light based on the scattered light detected by the detection unit, wherein the irradiation unit irradiates an irradiation light of s-polarization at a small irradiation angle, and the determination unit determines that the cause of the scattered light is a foreign material when an intensity of the detected scattered light is great and that the cause of the scattered light is a microscopic defect when the intensity of the detected scattered light is small.

2. An apparatus for inspecting a surface of an object to be processed, comprising:
at least one irradiation unit for irradiating a light on the surface of the object;
at least one detection unit for detecting a light scattered from the surface of the object in response to the irradiated light; and
a determination unit for determining a cause of the scattered light based on the scattered light detected by the detection unit,
wherein the irradiation unit irradiates irradiation lights of s-polarization and p-polarization at a small irradiation angle, and the determination unit determines that the cause of the scattered light is a foreign material when a ratio of an intensity of the scattered light due to the irradiation light of s-polarization to an intensity of the scattered light due to the irradiation light of p-polarization is great and that the cause of the scattered light is a microscopic defect when the ratio is small.

3. The apparatus of claim 2, wherein the irradiation unit varies the irradiation angles of the irradiation lights from 15 to 45 degrees with respect to the surface of the object, and the determination unit determines that the cause of the scattered light is the foreign material when the ratio is greater than 1 and that the cause of the scattered light is the microscopic defect when the ratio is 1 or less.

4. An apparatus for inspecting a surface of an object to be processed, comprising:
at least one irradiation unit for irradiating a light on the surface of the object;
at least one detection unit for detecting a light scattered from the surface of the object in response to the irradiated light; and
a determination unit for determining a cause of the scattered light based on the scattered light detected by the detection unit,
wherein the irradiation unit is fixed to irradiate an irradiation light of s-polarization at a small irradiation angle, and the determination unit determines that the cause of the scattered light is a foreign material when an intensity of the detected scattered light is great and that the cause of the scattered light is a-microscopic defect when the intensity of the detected scattered light is small.

5. An apparatus for inspecting a surface of an object to be processed, comprising:
at least one irradiation unit for irradiating a light on the surface of the object;
at least one detection unit for detecting a light scattered from the surface of the object in response to the irradiated light; and
a determination unit for determining a cause of the scattered light based on the scattered light detected by the detection unit,
wherein the irradiation unit is fixed to irradiate irradiation lights of s-polarization and p-polarization at a small irradiation angle, and the determination unit determines that the cause of the scattered light is a foreign material when a ratio of an intensity of the scattered light due to the irradiation light of s-polarization to an intensity of the scattered light due to the irradiation light of p-polarization is great and that the cause of the scattered light is a microscopic defect when the ratio is small.

6. The apparatus of claim 5, wherein the irradiation unit is fixed to irradiate the irradiation lights at any angle of 15 to 45 degrees with respect to the surface of the object, and the determination unit determines that the cause of the scattered light is the foreign material when the ratio is greater than 1 and that the cause of the scattered light is the microscopic defect when the ratio is 1 or less.

7. An apparatus for inspecting a surface of an object to be processed, comprising:
at least one irradiation unit for irradiating a light on the surface of the object;
at least one detection unit for detecting a light scattered from the surface of the object in response to the irradiated light; and
a determination unit for determining a cause of the scattered light based on the scattered light detected by the detection unit,
wherein the irradiation unit irradiates an irradiation light of s-polarization at a small irradiation angle while the detection unit detects the scattered light at a small scattering angle, and the determination unit determines that the cause of the scattered light is a foreign material when the detected scattered light has a great amplitude and that the cause of the scattered light is a microscopic defect when the detected scattered light has a small amplitude.

8. An apparatus for inspecting a surface of an object to be processed, comprising:
at least one irradiation unit for irradiating a light on the surface of the object;
at least one detection unit for detecting a light scattered from the surface of the object in response to the irradiated light; and
a determination unit for determining a cause of the scattered light based on the scattered light detected by the detection unit,
wherein the irradiation unit irradiates an irradiation light of p-polarization at a large irradiation angle while the detection unit detects the scattered light at a large scattering angle, and the determination unit determines that the cause of the scattered light is a microscopic defect when the detected scattered light has a great amplitude and that the cause of the scattered light is a foreign material when the detected scattered light has a small amplitude.

9. An apparatus for inspecting a surface of an object to be processed, comprising:
at least one irradiation unit for irradiating a light on the surface of the object;
at least one detection unit for detecting a light scattered from the surface of the object in response to the irradiated light; and
a determination unit for determining a cause of the scattered light based on the scattered light detected by the detection unit,
wherein the irradiation unit irradiates irradiation lights of s-polarization and p-polarization while varying irradiation angles thereof, and the determination unit determines that the cause of the scattered light is a foreign material when an amplitude of the scattered light at a small scattering angle due to the irradiation light of s-polarization at a small irradiation angle is great and that the cause of the scattered light is a microscopic defect when an amplitude of the scattered light at a large scattering angle due to the irradiation light of p-polarization at a large irradiation angle is great.

10. The apparatus of claim 9, wherein the determination unit determines that the cause of the scattered light is the foreign material when the amplitude of the scattered light due to the irradiation light of s-polarization has a peak value at a scattering angle of 20 degrees or thereabout with respect to the surface of the object and that the cause of the scattered light is a microscopic defect when the amplitude of the scattered light due to the irradiation light of p-polarization has a peak value at a scattering angle of 90 degrees or thereabout with respect to the surface of the object.

11. An apparatus for inspecting a surface of an object to be processed, comprising:
   at least one irradiation unit for irradiating a light on the surface of the object;
   at least one detection unit for detecting a light scattered from the surface of the object in response to the irradiated light; and
   a determination unit for determining a cause of the scattered light based on the scattered light detected by the detection unit,
   wherein the irradiation unit is fixed to irradiate an irradiation light of s-polarization at a small irradiation angle while the detection unit is fixed to detect the scattered light at a small scattering angle, and the determination unit determines that the cause of the scattered light is a foreign material when the detected scattered light has a great amplitude and that the cause of the scattered light is a microscopic defect when the detected scattered light has a small amplitude.

12. An apparatus for inspecting a surface of an object to be processed, comprising:
   at least one irradiation unit for irradiating a light on the surface of the object;
   at least one detection unit for detecting a light scattered from the surface of the object in response to the irradiated light; and
   a determination unit for determining a cause of the scattered light based on the scattered light detected by the detection unit,
   wherein the irradiation unit is fixed to irradiate an irradiation light of p-polarization at a large irradiation angle while the detection unit is fixed to detect the scattered light at a large scattering angle, and the determination unit determines that the cause of the scattered light is a microscopic defect when the detected scattered light has a great amplitude and that the cause of the scattered light is a foreign material when the detected scattered light has a small amplitude.

13. An apparatus for inspecting a surface of an object to be processed, comprising:
   at least one irradiation unit for irradiating a light on the surface of the object;
   at least one detection unit for detecting a light scattered from the surface of the object in response to the irradiated light; and
   a determination unit for determining a cause of the scattered light based on the scattered light detected by the detection unit,
   wherein the irradiation unit irradiate the irradiation light of s-polarization at a small irradiation angle and the irradiation light of p-polarization at a large irradiation angle while the detection unit is fixed to detect the scattered lights at a large and a small scattering angle, respectively, and the determination unit determines that the cause of the scattered light is a foreign material when the scattered light of the small scattering angle due to the irradiation light of s-polarization has a great amplitude and that the cause of the scattered light is a microscopic defect when the scattered light of the large scattering angle due to the irradiation light of p-polarization has a great amplitude.

* * * * *